(12) United States Patent
Benner

(10) Patent No.: US 7,741,294 B1
(45) Date of Patent: Jun. 22, 2010

(54) NON-STANDARD NUCLEOBASES IMPLEMENTING THE ISOCYTIDINE AND ISOGUANOSINE HYDROGEN BONDING PATTERNS

(76) Inventor: Steven Albert Benner, 1501 NW. 68th Ter., Gainesville, FL (US) 32605-4147

( * ) Notice: Subject to any disclaimer, the term of this patent is extended or adjusted under 35 U.S.C. 154(b) by 900 days.

(21) Appl. No.: 11/371,756

(22) Filed: Mar. 9, 2006

Related U.S. Application Data

(60) Provisional application No. 60/680,817, filed on May 14, 2005.

(51) Int. Cl.
*A01N 43/04* (2006.01)
*C07H 21/02* (2006.01)
*C07H 7/06* (2006.01)

(52) U.S. Cl. .................. 514/23; 536/23.1; 536/29.2

(58) Field of Classification Search .................. None
See application file for complete search history.

(56) References Cited

U.S. PATENT DOCUMENTS 6,001,983 A * 12/1999 Benner .................. 536/23.1
6,140,496 A * 10/2000 Benner .................. 536/27.1
6,600,028 B1 * 7/2003 Brown et al. .................. 536/23.1

OTHER PUBLICATIONS

Seela et al., "7-Deazaisoguanisine quartets", Chemical Communications, 1997, 1869-70, vol. 19.*
Voegel, Von Krosigk, Benner (1993) Synthesis & tautomeric equilibrium of 6-amino-5-benzyl-3-methylpyrazin-2-one. J. Org. Chem. 58, 7542-7.
Krosigk, Benner (1995) pH-independent triple helix formation by an oligonucleotide containing a pyrazine donor-donor-acceptor base. J. Am. Chem. Soc. 117, 5361-5362.
Havemann, Hoshika, Hutter, Benner (2008) Incorporation of multiple sequential pseudothymides by DNA polymerases & their impact. Nucleos.Nucleot. Nucl. Acids 27, 261-8.

* cited by examiner

Primary Examiner—Traviss C McIntosh, III

(57) ABSTRACT

This invention provides compositions of matter that, when incorporated into an oligonucleotide, present to a complementary strand in a Watson-Crick pairing geometry a pattern of hydrogen bonds that is different from the pattern presented by adenine, guanine, cytosine, and thymine. Most specifically, this invention discloses and claims compositions of matter that present the same hydrogen bonding patterns as the isocytidine and isoguanosine nucleobases, but do not have unfavorable tautomeric forms, do not become disassociated from their sugar, and do not make major groove interactions, as much, as easily, or as strongly as isocytidine and isoguanosine.

3 Claims, 13 Drawing Sheets

NON-STANDARD NUCLEOBASES IMPLEMENTING THE ISOCYTIDINE AND ISOGUANOSINE HYDROGEN BONDING PATTERNS

This application claims the benefit of U.S. Provisional Patent Application Ser. No. 60/680,817, filed May 14, 2005.

FIELD

This invention relates to the field of nucleic acid chemistry, more specifically to the field of nucleic acid analogs, and most specifically to oligonucleotide analogs that incorporate non-standard nucleobases, those that present to a complementary strand in a Watson-Crick pairing geometry a pattern of hydrogen bonds that is different from the pattern presented by adenine, guanine, cytosine, and thymine.

BACKGROUND

Natural oligonucleotides bind to complementary oligonucleotides according to the well-known rules of nucleobase pairing first elaborated by Watson and Crick in 1953, where adenine (A) pairs with thymine (T) (or uracil, U, in RNA), and guanine (G) pairs with cytosine (C), with the complementary strands anti-parallel to one another. In this disclosure, "DNA" or "nucleic acid" is understood to include, as appropriate, both DNA (where the sugar is 2'-deoxyribose) and RNA (where the sugar is ribose), as well as derivatives where the sugar is modified, as in 2'-O-methyl, 2'-O-allyl, 2'-deoxy-2'-fluoro, and 2',3'-dideoxynucleoside derivatives, nucleic acid analogs based on other sugar backbones, such as threose, locked nucleic acid derivatives, bicyclo sugars, or hexose, glycerol and glycol sugars [Zhang, L., Peritz, A., Meggers, E. (2005) A simple glycol nucleic acid. *J. Am. Chem. Soc.* 127, 4174-4175], nucleic acid analogs based on non-ionic backbones, such as "peptide nucleic acids", these nucleic acids and their analogs in non-linear topologies, including as dendrimers, comb-structures, and nanostructures, and these nucleic acids and their analogs carrying tags (e.g., fluorescent, functionalized, or binding) to the ends, sugars, or nucleobases.

These pairing rules allow for the specific hybridization of an oligonucleotide to a complementary oligonucleotide, making oligonucleotides valuable as probes in the laboratory, in diagnostic applications, as messages that can direct the synthesis of specific proteins, and in a wide range of other applications well known in the art. Such base pairing is used, for example and without limitation, to capture other oligonucleotides to beads, arrays, and other solid supports, to allow nucleic acids to fold in hairpins, beacons, and catalysts, as supports for functionality, such as fluorescence, fluorescence quenching, binding/capture tags, and catalytic functionality, as part of more complex architectures, including dendrimers and nanostructures, and as scaffolds to guide chemical reactions.

Further, nucleobase pairing is the basis by which enzymes are able to catalyze the synthesis of new oligonucleotides that are complementary to template nucleotides. In this synthesis, building blocks (normally the triphosphates of ribo- or deoxyribonucleosides carrying of A, T, U, C, or G) are directed by a template oligonucleotide to form a complementary oligonucleotide with the complementary sequence. This process is the basis for replication of all forms of life, and also serves as the basis for technologies for enzymatic synthesis and amplification of specific heterosequence nucleic acids by enzymes such as DNA and RNA polymerase, in the polymerase chain reaction (PCR), and in a variety of architectures that may involve synthesis, ligation, cleavage, immobilization and release, inter alfa, used in technology to detect nucleic acids.

Nucleobase pairing following rules of complementarity is known to be useful in a variety of architectures. In solution, nucleobase pairing in the loop of a molecular beacon can open the beacon, separating a fluorescent species attached to one end of a hairpin structure from a quencher on the other. Pairing can assemble two DNA fragments transiently or covalently, as in a template-directed ligation. Pairing is useful for affixing an oligonucleotide that is free in solution to a support carrying the complementary oligonucleotide. The oligonucleotide can carry functional groups, including fluorescent groups attached to the nucleobases.

The Watson-Crick pairing rules can be understood chemically in terms of the arrangement of hydrogen bonding groups on the heterocyclic nucleobases of the oligonucleotide, groups that can either be hydrogen bond donors or acceptors. In the standard Watson-Crick geometry, a large purine nucleobase pairs with a small pyrimidine nucleobase. Thus, the AT nucleobase pair is the same size as a GC nucleobase pair. This means that the rungs of the DNA ladder, formed from either AT or GC nucleobase pairs, all have the same length.

Further recognition between nucleobases is determined by hydrogen bonds between the nucleobases. In standard nucleobases, hydrogen bond donors are heteroatoms (nitrogen or oxygen in the natural nucleobases) bearing a hydrogen, hydrogen bond acceptors are heteroatoms (nitrogen or oxygen in the natural nucleobases) with a lone pair of electrons. In the geometry of the Watson-Crick nucleobase pair, a six membered ring (in standard nucleobases, a pyrimidine) is juxtaposed to a ring system composed of a fused six membered ring and a five membered ring (in standard nucleobases, a purine), with a middle hydrogen bond linking two ring atoms, and hydrogen bonds on either side joining functional groups appended to each of the rings, with donor groups paired with acceptor groups.

In many applications, the nucleobases incorporated into one or more oligonucleotide analogs carry an appendage. In standard nucleobases, the appendage, or side chain, is attached to one or more pyrimidines at the 5-position, or at the 7-position of a 7-deazapurine, or to an exocyclic nitrogen, most often the exocyclic amino group of adenine or cytosine. Such nucleoside analogs have application because of their combination of Watson-Crick nucleobase pairing ability and the properties or reactivities associated with species appended via the side chain. For example, oligonucleotides containing a T to which is appended a side chain bearing a biotin residue can first bind to a complementary oligonucleotide, and the hybrid can then be isolated by virtue of the specific affinity of biotin to avidin [Langer, P. R., Waldrop, A. A., Ward, D. C. (1981) *Proc. Nat. Acad. Sci.* 78, 6633-6637]. This finds application in diagnostic work. Instead of biotin, the side chain can carry a fluorescent moiety, or a moiety that quenches the fluorescence of another moiety, a branching point, or a moiety that complexes to a metal, or a moiety that confers catalytic activity on the oligonucleotide, or a moiety that assists in the attachment of the oligonucleotide analog to a solid support, such as a bead, a one dimensional array, or a two dimensional array.

Often, derivatized standard nucleotides can be incorporated into oligonucleotides by enzymatic transcription of natural oligonucleotide templates in the presence of the triphosphate of the derivatized nucleoside, the substrate of the appropriate (DNA or RNA) polymerase, or a reverse transcriptase. In this process, a natural nucleoside is placed in the template, and standard Watson-Crick nucleobase pairing is exploited to direct the incoming modified nucleoside opposite to it in the growing oligonucleotide chain.

The standard available nucleobase pairs are limited in that they make available only two mutually exclusive hydrogen bonding patterns. This means that should one wish to introduce a modified nucleoside based on one of the natural nucleosides into an oligonucleotide, it would be incorporated wherever the complementary natural nucleoside is found in the template. For many applications, this is undesirable.

Further, in many applications, it would be desirable to have nucleobase pairs that behave as predictably as the AT (or U) and GC nucleobase pairs, but that do not cross-pair with natural oligonucleotides, which are built from A, T (or U), G, and C. This is especially true in diagnostics assays based. Biological samples generally contain many nucleic acid molecules in addition to the nucleic acid that one wishes to detect. The adventitious DNA/RNA, often present in abundance over the targeted analyte DNA (or RNA), is also composed of A, T (or U), G, and C. Thus, adventitious DNA/RNA can compete with the desired interactions between two or more oligonucleotide-like molecules.

Many of the limitations that arise from the existence of only four standard nucleobases, joined in only two types of nucleobase pairs via only two types of hydrogen bonding schemes, could be overcome were additional nucleobases available that could be incorporated into oligonucleotides. Here, the additional nucleobases would still pair in the Watson-Crick geometry, but would present patterns of hydrogen bond donating and accepting groups in a pattern different from those presented by the natural nucleobases. They therefore would form nucleobase pairs with additional complementary nucleobases in preference to (and, preferably, with strong preference to, meaning with at least a 10 to 100 fold affinity greater than to mismatched oligonucleotides or oligonucleotide analogs).

In the last decade, Benner disclosed compositions of matter that were intended to overcome the limitations of molecular recognition by changing the pattern of hydrogen bond donor and acceptor groups presented by a nucleobase to the nucleobase on a complementary oligonucleotide analog [U.S. Pat. Nos. 5,432,272, 5,965,364, 6,001,983, 6,037,120, 6,140,496, 6,627,456, 6,617,106]. These disclosures showed that the geometry of the Watson-Crick nucleobase pair can accommodate as many as 12 nucleobases forming 6 mutually exclusive pairs. Of these, four nucleobases forming two pairs are "standard", while eight nucleobases forming four pairs were termed "non-standard". Adding the non-standard nucleobases to the standard nucleobases yielded an Artificially Expanded Genetic Information System (AEGIS). Specifically, the structures shown in FIG. 1, taken from U.S. Pat. No. 6,140,496, implement the designated hydrogen bonding patterns. It was also noted that these nucleobases analogs might be functionalized to enable a single biopolymer capable of both genetics and catalysis. Expanded genetic alphabets have now been further explored in a variety of laboratories, and the possibility of a fully artificial genetic system has been advanced [Switzer, C. Y., Moroney, S. E., Benner, S. A. (1989) Enzymatic incorporation of a new base pair into DNA and RNA. *J. Am. Chem. Soc.* 111, 8322-8323] [Piccirilli, J. A., Krauch, T., Moroney, S. E., Benner, S. A. (1990) Extending the genetic alphabet. Enzymatic incorporation of a new base pair into DNA and RNA. *Nature* 343, 33-37] [Piccirilli, J. A., Krauch, T., MacPherson, L. J., Benner, S. A. (1991) A direct route to 3-(ribofuranosyl)-pyridine nucleosides. *Helv. Chim. Acta* 74, 397-406] [Voegel, J. J., Altorfer, M. M., Benner, S. A. (1993) The donor-acceptor-acceptor purine analog. Transformation of 5-aza-7-deaza-isoguanine to 2'-deoxy-5-aza-7-deaza-iso-guanosine using purine nucleoside phosphorylase. *Helv. Chim Acta* 76, 2061-2069] [Voegel, J. J., von Krosigk, U., Benner, S. A. (1993) Synthesis and tautomeric equilibrium of 6-amino-5-benzyl-3-methylpyrazin-2-one. An acceptor-donor-donor nucleoside base analog. *J. Org. Chem.* 58, 7542-7547] [Heeb, N. V., Benner, S. A. (1994) Guanosine derivatives bearing an $N^2$-3-imidazolepropionic acid. *Tetrahedron Lett.* 35, 3045-3048] [Voegel, J. J., Benner, S. A. (1994) Non-standard hydrogen bonding in duplex oligonucleotides. The base pair between an acceptor-donor-donor pyrimidine analog and a donor-acceptor-acceptor purine analog. *J. Am. Chem. Soc.* 116, 6929-6930] [von Krosigk, U., Benner, S. A. (1995) pH-independent triple helix formation by an oligonucleotide containing a pyrazine donor-donor-acceptor base. *J. Am. Chem. Soc.* 117, 5361-5362] [Voegel, J. J., Benner, S. A. (1996) Synthesis, molecular recognition and enzymology of oligonucleotides containing the non-standard base pair between 5-aza-7-deaza-iso-guanine and 6-amino-3-methylpyrazin-2-one, a donor-acceptor-acceptor purine analog and an acceptor-donor-donor pyrimidine analog. *Helv. Chim. Acta* 79, 1881-1898] [Voegel, J. J., Benner, S. A. (1996) Synthesis and characterization of non-standard nucleosides and nucleotides bearing the acceptor-donor-donor pyrimidine analog 6-amino-3-methylpyrazin-2-one. *Helv. Chim. Acta* 79, 1863-1880] [Kodra, J., Benner, S. A. (1997) Synthesis of an N-alkyl derivative of 2'-deoxyisoguanosine. *Syn. Lett.*, 939-940] [Jurczyk, S., Kodra, J. T., Rozzell, J. D., Jr., Benner, S. A., Battersby, T. R. (1998) Synthesis of oligonucleotides containing 2'-deoxyisoguanosine and 2'-deoxy-5-methyliso-cytidine using phosphoramidite chemistry. *Helv. Chim. Acta* 81, 793-811] [Lutz, S., Burgstaller, P., Benner, S. A. (1999) An in vitro screening technique for polymerases that can incorporate modified nucleotides. Pseudouridine as a substrate for thermostable polymerases. *Nucl. Acids Res.* 27, 2792-2798] [Jurczyk, S. C., Battersby, T. R., Kodra, J. T., Park, J.-H., Benner, S. A. (1999) Synthesis of 2'-deoxy-isoguanosine triphosphate and 2'-deoxy-5-methyl-isocytidine triphosphate. *Helv. Chim. Acta.* 82, 1005-1015] [Jurczyk, S. C., Horlacher, J., Devine, K. G., Benner, S. A., Battersby, T. R. (2000) Synthesis and characterization of oligonucleotides containing 2'-deoxyxanthosine using phosphoramidite chemistry. *Helv. Chim. Acta* 83, 1517-1524] [Rao, P., Benner, S. A. (2001) A fluorescent charge-neutral analog of xanthosine: Synthesis of a 2'-deoxyribonucleoside bearing a 5-aza-7-deazaxanthine base. *J. Org. Chem.* 66, 5012-5015].

To systematize the nomenclature for the hydrogen bonding patterns, the hydrogen bonding pattern implemented on a small component of a nucleobase pair pare designated by the prefix "py". Following this prefix is the order, from the major groove to the minor groove, of hydrogen bond acceptor (A) and donor (D) groups. Thus, both thymine and uracil implement the standard hydrogen bonding pattern pyADA. The standard nucleobase cytosine implements the standard hydrogen bonding pattern pyDAA. Hydrogen bonding patterns implemented on the large component of the nucleobase pair are designated by the prefix "pu". Again following the prefix, the hydrogen bond donor and acceptor groups are designated, from the major to the minor grooves, using "A" and "D". Thus, the standard nucleobases adenine and guanine implement the standard hydrogen bonding patterns puDA- and puADD respectively.

A central teaching of this disclosure is that hydrogen bonding pattern designated using this systematic nomenclature is distinct, in concept, from the organic molecule that is used to implement the hydrogen bonding pattern. Thus, guanosine is a nucleoside that implements the puADD hydrogen bonding pattern. So does, however, 7-deazaguanosine, 3-deazaguanosine, 3,7-dideazaguanosine, and any of any number of other purines and purine derivatives, including those that carry side chains to which are appended functional groups, such as fluorescent, fluorescent quencher, attachment, or metal complexing groups. Which organic molecule is chosen to implement a specific hydrogen bonding pattern determines, in large part, the utility of the non-standard hydrogen bonding pattern, in various applications to which it might be applied.

The structures disclosed by U.S. Pat. No. 6,140,496, as well as its predecessor patents, provide for an expanded molecular recognition system by providing more than four independently recognizable building blocks that can be incorporated into DNA and RNA.

Should the additional nucleobase pairs be placed into DNA and RNA, and if once so placed they have the desirable pairing properties, chemical stability, and other features known to those skilled in they art, they could be useful for a variety of purposes. For example, RNA molecules prepared by transcription, although it is known to be a catalyst under special circumstances [Cech, T. R., Bass, B. L (1986). *Ann. Rev. Biochem.* 55, 599] [Szostak, J. W. (1986) Nature 332, 83. Been, M. D., Cech, T. R. (1988) *Science* 239, 1412], appear to have a much smaller catalytic potential than proteins because they lack building blocks bearing functional groups. Conversely, the limited functionality present on natural oligonucleotides constrains the chemist attempting to design catalytically active RNA molecules, in particular, RNA molecules that catalyze the template-directed polymerization of RNA.

Likewise, additional nucleobase pairs can be incorporated enzymatically at specific positions in an oligonucleotide molecule [Switzer, C. Y., Moroney, S. E., Benner, S. A. (1989) *J. Am. Chem. Soc.* 111, 8322]. If functionalized, such additional nucleobases should also allow the incorporation of functional groups into specific positions in a DNA or RNA sequence. A polymerase chain reaction has been demonstrated using a variant of an HIV reverse transcriptase to incorporate the pair between 2,4-diamino-5-(1'-beta-D-2'-deoxyribofuranosyl)-pyrimidine, implementing the pyDAD hydrogen bonding pattern, and 3,9-dihydro-9-(1'-beta-D-2'-deoxyribofuranosyl)-1H-purine-2,6-dione, implementing the puADA hydrogen bonding pattern [Sismour, A. M., Lutz, S., Park, J.-H., Lutz, M. J., Boyer, P. L., Hughes, S. H., Benner, S. A. (2004) PCR amplification of DNA containing non-standard base pairs by variants of reverse transcriptase from human immunodeficiency virus-1. *Nucl. Acids. Res.* 32, 728-7351. As standard nucleobases bearing functional groups at the 5-position of the uridine ring are accepted as substrates for most polymerases [Leary, J. L., Brigati, D. J., Ward, D. C. (1983) *Proc. Natl. Acad. Sci.* 80, 4045], non-standard nucleobases that are modified at the analogous positions are also accepted, provided that the polymerase accepts the parent non-standard nucleobase. New nucleobase pairs should also find use in studies of the structure of biologically important RNA and DNA molecules [Chen, T. R., Churchill, M. E. A. Tullius, T. D. Kallenbach, N. R., Seemann, N. C. (1988) *Biochem.* 27, 6032] and protein-nucleic acid interactions. They should also be useful in assembling nanostructures, including branched DNA useful for diagnostics, or for nanomachines. Further, non-standard nucleobases can be used to expand the genetic code, increasing the number of amino acids that can be incorporated translationally into proteins [Bain, J. D., Chamberlin, A. R., Switzer, C. Y., Benner, S. A. (1992) Ribosome-mediated incorporation of non-standard amino acids into a peptide through expansion of the genetic code. *Nature* 356, 537-539].

Some commercial applications have already been realized with the expanded genetic information systems disclosed by Benner in his patents. For example, the nucleobase pair between 2-amino-5-methyl1-(1'-beta-D-2'-deoxyribofuranosyl)-4(1H)-pyrimidinone, also known as 2'-deoxyisocytidine, disoC, or sometimes (less correctly) isoC and implementing the pyAAD hydrogen bonding pattern, and 6-amino-1,9-dihydro-9-(1'-beta-D-2'-deoxyribofuranosyl)-3H-purin-2-one, also known as 2'-deoxyisoguanosine, disoG, or sometimes (less correctly) isoG, and implementing the puDDA hydrogen bonding pattern, is incorporated into the branched DNA diagnostics tools marketed today by Bayer. Here, it provides molecular recognition on demand in aqueous solution, similar to nucleic acids but with a coding system that is orthogonal to the system in DNA and RNA, Thus, it prevents the assembly of the branched dendrimer in the assay from being inhibited by adventitious nucleic acid, and prevents adventitious nucleic acid from capturing signaling elements form the nanostructure in the absence of the target analyte nucleic acid, creating noise. Further, adding extra letters to the genetic alphabet speeds hybridization, presumably because it decreases the number of close mismatches where DNA dwells before finding its correct, fully matched partner. The branched DNA assay now has FDA-approval, and is widely used to provide personalized patient care in the clinic.

The Benner patents claimed a wide range of structures generally, but only a few specifically. The compounds specifically claimed, where those claims were supported by specific examples in the disclosure, were disclosed as the preferred implementations of the individual hydrogen bonding patterns, and are reproduced in FIG. 1 (taken from FIG. 2 of U.S. Pat. No. 6,140,496). Making reference to U.S. Pat. No. 6,140,496, the following implementations (where a systematic name is given for the 2'-deoxyribonucleoside, the corresponding ribonucleosides, 2'-O-methyl ribonucleosides, and various derivatives of these were also disclosed) were preferred as implementations for each of the hydrogen bonding patterns:

For the pyDAD hydrogen bonding pattern. The preferred embodiment disclosed in U.S. Pat. No. 6,140,496 supported the pyDAD hydrogen bonding pattern on the 2,4-diaminoypyrimidine heterocycle. The specific deoxyribonucleoside was 2,4-diamino-5-(1'-beta-D-2'-deoxyribofuranosyl)-pyrimidine, also named (1R)-1,4-anhydro-2-deoxy-1-C-(2,4-diamino-5-pyrimidinyl)-D-erythropentitol.

For the puADA hydrogen bonding pattern. The preferred embodiment disclosed in U.S. Pat. No. 6,140,496 supported the pyDAD hydrogen bonding pattern on the xanthine heterocycle. The specific deoxyribonucleoside was 3,9-dihydro-9-(1'-beta-D-2'-deoxyribofuranosyl)-1H-purine-2,6-dione, also known as 9-(2'-deoxy-beta-D-ribosyl)-xanthine.

For the pyAAD hydrogen bonding pattern. The preferred embodiment disclosed in U.S. Pat. No. 6,140,496 supported the pyDAD hydrogen bonding pattern on the 5-methyl-isocytosine heterocycle. The specific deoxyribonucleoside was 2-amino-5-methyl-1-(1'-beta-D-2'-deoxyribofuranosyl)-4(1H)-pyrimidinone, For the puDDA hydrogen bonding pattern. The preferred embodiment disclosed in U.S. Pat. No. 6,140,496 supported the pyDAD hydrogen bonding pattern on the isoguanine heterocycle. The specific deoxyribonucleoside was 6-amino-1,9-dihydro-9-(1'-beta-D-2'-deoxyribofuranosyl)-3H-purin-2-one.

For the pyDDA hydrogen bonding pattern. The preferred embodiment disclosed in U.S. Pat. No. 6,140,496 supported the pyDAD hydrogen bonding pattern on the 6-amino-5-methyl-2(1H)-pyrazinone heterocycle. The specific deoxyribonucleoside was 6-amino-5-methyl-3-(1'-beta-D-2'-deoxyribofuranosyl)-2(1H)-pyrazinone.

For the puAAD hydrogen bonding pattern. The preferred embodiment disclosed in U.S. Pat. No. 6,140,496 supported the pyDAD hydrogen bonding pattern on the 5-aza-3,7-dideazaguanosine heterocycle. The specific deoxyribonucleoside was 2-amino-1,9-dihydro-5-aza-3,7-dideaza-9-(1'-beta-D-2'-deoxyribofuranosyl)-1H-purin-6-one, also known as 7-amino-9-(1'-beta-D-2'-deoxyribofuranosyl)-imidazo[1,2-c]pyrimidin-5(1H)-one, For the pyADD hydrogen bonding pattern. The preferred embodiment disclosed in U.S. Pat. No. 6,140,496 supported the pyDAD hydrogen bonding pattern on the 6-amino-3-methyl-2(1H)-pyrazinone heterocycle. The specific deoxyribonucleoside was 6-amino-3-methyl-5-(1'-beta-D-2'-deoxyribofuranosyl)-2(1H)-pyrazinone, For the puDAA hydrogen bonding pattern. The preferred embodiment disclosed in U.S. Pat. No. 6,140,496 supported the pyDAD hydrogen bonding pattern on the 4-amino-1,3,5-triazin-2(8H)-one heterocycle. The specific deoxyribonucleoside was 4-amino-8-(2-deoxy-beta-D-erythro-pentofuranosyl)-imidazo[1,2-a]-1,3,5-triazin-2(8H)-one, also known as, 4-amino-8-(1'-beta-D-2'-deoxyribofuranosyl)-imidazo[1,2-a]-1,3,5-triazin-2(8H)-one.

Despite the value of the compositions disclosed by U.S. Pat. No. 6,140,496, it is clear that the specific compositions used to implement the various non-standard hydrogen bonding patterns were not optimal, at least from the perspective of potential utility. Several problematic physical and chemical properties of the compositions that were claimed specifically were disclosed in the specification of U.S. Pat. No. 6,140,496.

For example, the nucleobases that were, in U.S. Pat. No. 6,140,496, specifically disclosed as implementations of the pyADD and pyDDA hydrogen bonding patterns undergo an epimerization reaction that interconverts the beta and alpha anomers [von Krosigk, U., Benner, S. A. (1995) pH-independent triple helix formation by an oligonucleotide containing a pyrazine donor-donor-acceptor base. *J. Am. Chem. Soc.* 117, 5361-5362] [Vogel, J. J., von Krosigk, U., Benner, S. A. (1993) Synthesis and tautomeric equilibrium of 6-amino-5-benzyl-3-methylpyrazin-2-one. An acceptor-donor-donor nucleoside base analog. *J. Org. Chem.* 58, 7542-7547]. This is illustrated in FIG. 2.

It was noted that this epimerization diminished the utility of these nucleobases. U.S. Pat. No. 6,140,496 and its predecessors proposed to solve the epimerization problem by replacing the furanose ring system (which includes an oxygen in a ring) with a carbocyclic cyclopentane derivative (which does not, and therefore cannot epimerize). The carbocyclic nucleoside analog is, however, difficult to synthesize, and has other disadvantages, and has never been incorporated into a commercial product.

An alternative tactic proposed to manage the epimerization problem has the pyrazine heterocycles that were the preferred implementations of the pyDDA and pyADD hydrogen bonding implementations (respectively) attached to a ribose derivative where a lower alkyl, most preferably methyl, group is attached to the 2'-oxygen. The 2'-O-alkyl group is large, and it was proposed that although the undesired epimerization reaction interconverting the beta and alpha anomers would still occur, steric factors would cause the beta (desired) form to predominate at equilibrium. Again, this would create problems if multiple non-standard nucleobases implementing this hydrogen bonding pattern were incorporated into an oligonucleotide analog.

The specification of U.S. Pat. No. 6,140,496 and its predecessors, as well as the literature, disclose difficulties with the use of 6-amino-1,9-dihydro-9-(1'-beta-D-2'-deoxyribofuranosyl)-3H-purin-2-one (isoguanosine, or isoG) as the implementation of the puDDA hydrogen bonding pattern. In its major keto form, isoguanosine implements the desired puDDA hydrogen bonding pattern. Isoguanosine has long been known to exist, to about 10% of the total in water, in a minor enolic tautomeric form. The enolic tautomer presents the puDAD hydrogen bonding pattern that is complementary to the thymidine and uridine nucleobases. That is, about 10% of isoguanine presents the puDAD hydrogen bonding pattern, not the desired puDDA pattern. While the presence of the minor tautomer does not adversely affect the use of isoguanosine in some applications, it does lower its utility in many others. In particular, it does inconvenience some polymerases that prefer to place thymidine (T) and/or uridine (U), rather than isocytidine (isoC), opposite isoguanosine in a template.

The disutility of this was recently shown by Johnson et al. [Johnson, S. C., Sherrill, C. B., Marshall, D. J., Moser, M. J., Prudent, J. R. (2004) A third base pair for the polymerase chain reaction: inserting isoC and isoG. *Nucl. Acids Res.* 32, 1937-1941], who attempted to do a polymerase chain reaction amplification of a DNA molecule, requiring the repeated copying of the isoguanine-isocytosine nucleobase pair implementing the puDDA-pyAAD hydrogen bonding patterns. As expected from the known tautomeric behavior of isoguanine, the isoG-isoC pair was lost during the PCR reaction, presumably due to mismatching between T and the minor tautomer of isoguanosine.

Other features of the compounds that were specifically disclosed in U.S. Pat. No. 6,140,496 and its predecessors as the preferred implementations of the various hydrogen bonding schemes narrow the scope of their utility. For example, the heterocycle of 3,9-dihydro-9-(1'-beta-D-2'-deoxyribofuranosyl)-1H-purine-2,6-dione heterocycle (xanthine) proposed to implement the puADA hydrogen bonding pattern, is an acid, having a plc between 5 and 6. Thus, at neutral pH and higher, where many polymerases operate and where many applications of oligonucleotide analog recognition are desired, xanthine is deprotonated. Deprotonation creates a negative charge, which destabilizes the duplex structure [Geyer, C. R., Battersby, T. R., Benner, S. A. (2003) Nucleobase pairing in expanded Watson-Crick like genetic information systems. The nucleobases. *Structure* 11, 1485-1498]. It is considered unlikely that multiple xanthines in an oligonucleotide analog would support rule-based molecular recognition effectively.

Likewise, the 2,4-diamino-5-(1'-beta-D-2'-deoxyribofuranosyl)-pyrimidine proposed to implement the pyDAD hydrogen bonding pattern carries a positive charge at pH 7.0, as it is a relatively good base. Further, the synthesis of the 2'-deoxyribonucleoside bearing this nucleobase is long and expensive.

Likewise, the specifically disclosed nucleoside analogs that implement the puAAD hydrogen bonding pattern on the 5-aza-3,7-dideazaguanosine heterocycle may be poor substrates for many DNA and RNA polymerases, especially those that make contact to an unshared pair of electrons in the minor groove [Steitz, T. in Burnett, R. M. and Vogel, H. J. (eds.) *Biological Organization: Macromolecular Interactions at High Resolution*, Academic Press: New York, 1987, pp. 45-55.1. This limits the utility of triphosphates of nucleoside analogs bearing this heterocycle as a substrate for a DNA polymerase, an RNA polymerase, and reverse transcriptases, as well as the utility of oligonucleotide analogs carrying this heterocycle as templates for these enzymes. This is also the case for derivatives which attach an alkyl group to the N-3 of the purine or purine analogs (in the analogous positions). In U.S. Pat. No. 6,140,496 and its predecessors, various N-3 methylated purines are disclosed as implementations of various hydrogen bonding patterns.

Likewise, the implementation of the pyAAD hydrogen bonding pattern using 5-alkylisocytidine derivatives proves to present difficulties. Deoxyribosides bearing the 2-amino-5-methyl-1-(1'-beta-D-2'-deoxyribofuranosyl)-4(1H)-pyrimidinone (also know as 5-methylisocytosine) is sensitive to depyrimidinylation, the cleavage of the 1-1' nitrogen-carbon bond to separate the heterocycle from the sugar, under acidic conditions. Considerable effort was devoted to developing the delicate synthetic procedures needed to prepare oligonucleotide analogs that contain multiple 2-deoxyisocytidines, increasing the expense of the synthesis. The acid sensitivity extends to the oligonucleotides in solution, diminishing their utility.

One purpose of the instant disclosure is to provide nucleobase analogs (where "nucleobase" refers to the heterocycle, or aglycone) that implement non-standard hydrogen bonding patterns, said analogs having properties improved over those analogs of the prior art that implement their respective hydrogen bonding patterns. In particular, the compositions of the instant invention mitigate or avoid entirely the limitations listed above of the compositions that were disclosed in U.S. Pat. No. 6,140,496.

One of ordinary skill in the art would find these improved properties unexpected, even in the light of the disclosures in patents and other literature of the prior art, and that find unexpected the greater utility that these nucleobase analogs have compared to the compositions disclosed in the prior art to implement this hydrogen bonding pattern.

Another purpose of the instant disclosure is to provide nucleoside analogs (where "nucleoside analog" is an analog of the heterocycle together with the sugar or sugar analog) that carry the nonstandard nucleobase analog, where the sugar is 2'-deoxyribose or ribose, as well as analogs where the sugar is modified, as in 2'-O-methyl, 2'-O-allyl, 2'-deoxy-2'-fluoro, and 2',3'-dideoxynucleoside derivatives, as well as nucleoside analogs based on other sugar backbones, such as threose, locked nucleic acid derivatives, bicyclo sugars, or hexose, glycerol and glycol sugars [Zhang, L., Peritz, A., Meggers, E. (2005) A simple glycol nucleic acid. *J. Am. Chem. Soc.* 127, 4174-4175].

Another purpose of the instant invention is to provide oligonucleotide analogs that incorporate one or more of the nonstandard nucleoside analogs. These include nucleic acid analogs that incorporate the sugars and sugar analogs mentioned in the previous paragraph, as well as oligonucleotide analogs based on non-ionic backbones, such as "peptide nucleic acids".

Another purpose of the instant invention is to provide nucleoside analogs in protected form that are suitable as precursors for the non-enzymatic synthesis of the non-standard oligonucleotide analogs.

Another purpose of the instant invention is to provide various phosphorylated derivatives of the stated nucleoside analogs, including triphosphates, which have utility in various enzymatic processes for the synthesis of the oligonucleotide analogs stated above.

Another purpose of the instant invention is to provide derivatives of the nucleoside analogs stated above that are degradation products of the oligonucleotide analogs stated above, and therefore help (for example) analyze these.

Another purpose of the instant invention is to provide 2',3'-dideoxy analogs of the nucleoside analogs mentioned above, 3'-ONH$_2$ derivatives, and other analogs and derivatives useful for the purpose of sequencing the oligonucleotide analogs mentioned above.

Another purpose of the instant invention is to provide compositions of matter wherein the oligonucleotide analogs mentioned above are attached to a solid phase, including a bead or microsphere, a two dimensional surface as part of a two dimensional array, and in a one dimensional array.

Another purpose of the instant invention is to provide processes for synthesizing said oligonucleotide analogs, both through template-directed polymerization and non-template-directed polymerization.

Another purpose of the instant invention is to provide processes for utilizing the compositions of matter described above. These include a variety of architectures that exploit a process that binds the stated oligonucleotide analogs to complementary oligonucleotide analogs containing one or more nucleobases that implements the complementary non-standard hydrogen bonding pattern, following an expanded set of Watson-Crick rules involving 6, 8, 10, and 12 letter DNA/RNA alphabets. These architectures include (without limitation) the stated oligonucleotide analogs as parts of compositions of matter that are beacons, nanostructures, dendrimers, and branched DNA molecules, and attached to solid supports such as beads, one dimensional arrays, two dimensional arrays, polonies, standard gels, and thermoresponsive gels, or in solution.

Another purpose of the instant invention is to provide oligonucleotide analogs as mentioned above for use in various architectures for detecting and sequencing oligonucleotides and oligonucleotide analogs, including within molecular beacons, in one and two dimensional arrays, on beads, in dendrimers that include both branched DNA and dendrimeric structures incorporating non-nucleosidic branching units, in assays involving cleavage reactions, in taggants and taggant detection schemes, and in nanostructures.

Another purpose of the instant invention is to provide the processes for utilization of the above described oligonucleotide analogs in the architectures above.

Another purpose of the instant invention is to provide functionalized derivatives of the nucleoside analogs mentioned above, carrying appendages that are fluorescent or that quench fluorescence, that assist in immobilization, that provide metal coordination sites, and that catalyze reactions, inter alia, when incorporated into the oligonucleotide analogs mentioned above, and into the processes mentioned above.

Another purpose of the instant invention is to provide processes for the repeated copying of the stated oligonucleotide analogs using template-directed polymerization, and copying of the copies in a polymerase chain reaction, having utility in oligonucleotide analog amplification, detection, and in vitro evolution to generate aptamers and oligonucleotide catalysts.

Another purpose of the instant invention is to provide non-standard nucleobases that are easily incorporated by DNA polymerases, RNA polymerases, and reverse transcriptases into the products of template-driven oligonucleotide synthesis. Various analyses of the interaction between polymerases and their substrates suggest that the polymerase seeks two unshared pairs of electrons in the minor groove, at position 3 of the purine (or analog) and at position 2 of the pyrimidine (or analog) [Steitz, T. in Burnett, R. M. and Vogel, H. J. (eds.) *Biological Organization: Macromolecular Interactions at High Resolution*, Academic Press: New York, 1987, pp. 45-55]. In addition, the base pairs that form three hydrogen bonds are expected to contribute more to duplex stability than pairs joined by just two hydrogen bonds.

These conditions are fulfilled for the compounds disclosed herein for implementing the pyDDA:puAAD hydrogen bonding pattern.

DESCRIPTION OF INVENTION

The purpose of the instant invention is to provide for new compositions of matter that can form nucleobase pairs, where the compositions implement the puDDA:pyAAD hydrogen bonding patterns. To this purpose, the instant invention provides compositions of matter that implement the pyAAD hydrogen bonding pattern in a form that is stable to depyrimidinylation.

The fact that 2-amino-5-methyl-1-(1'-beta-D-2'-deoxyribofuranosyl)-4(1H)-pyrimidinone is subject to depyrimidinylation under mildly acidic conditions at moderate temperatures has been known now in the art for a number of years. In this undesirable depyrimidinylation reaction, the carbon-nitrogen bond is cleaved, and the heterocycle separates from the sugar. This depyrimidinylation reaction greatly diminishes the utility of this heterocycle as a part of an expanded genetic alphabet. Because of this, protecting groups for the heterocycle must be chosen carefully for the solid phase synthesis of oligonucleotide analogs incorporating this nucleobase analog. Likewise, the oligonucleotide analogs that incorporate this nucleobase analog are easily sensitive to acidic cleavage.

Figure 1:
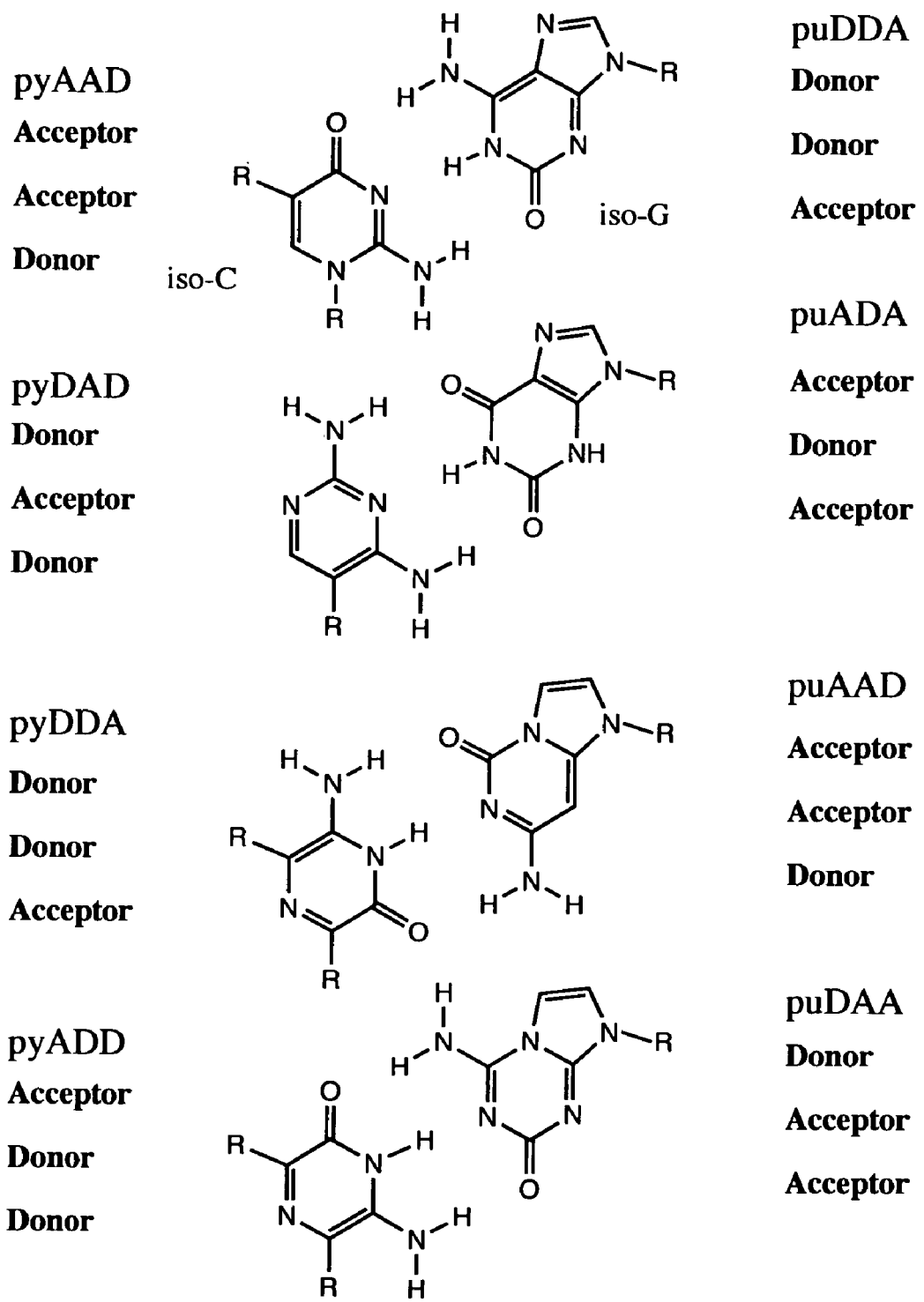
FIG. 1. From U.S. Pat. No. 6,140,496, the specific compositions of matter used to implement different hydrogen bonding patterns of the expanded genetic alphabet.
Figure 2:
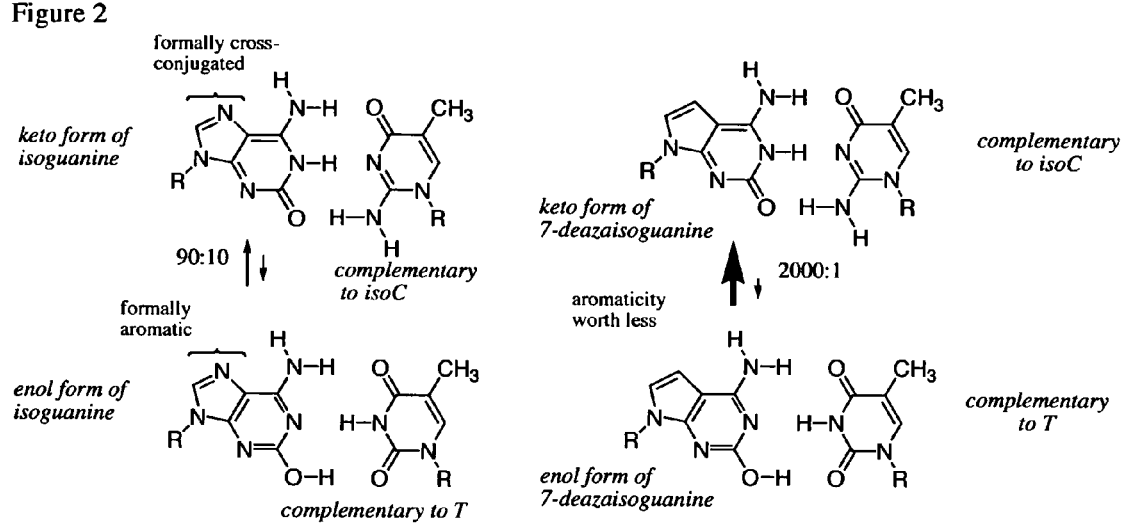
FIG. 2. Isoguanosine, a purine (pu) can generate two possible tautomers, an enol tautomer (giving a puDAD form, which will pair with T or U) or a keto tautomer (giving a puDDA form, which will pair with isoC). The extent of this tautomerism has been reported to be 10:1 in favor of the keto form.

While not wishing to be bound by theory, the Inventor reasoned that the instability of 2-amino-5-methyl-1-(1'-beta-D-2'-deoxyribofuranosyl)-4(1H)-pyrimidinone would not be present in 4-amino-1-alkyl-5-(1'-beta-D-2'-deoxyribofuranosyl)-2(1H)-pyrimidinone derivatives (FIG. 2). This is because the heterocycle is joined to the sugar via a carbon-carbon bond. Undesirable epimerization and undesirable tautomeric ambiguity would be avoided by the 1-alkyl substituents.

Figure 3:
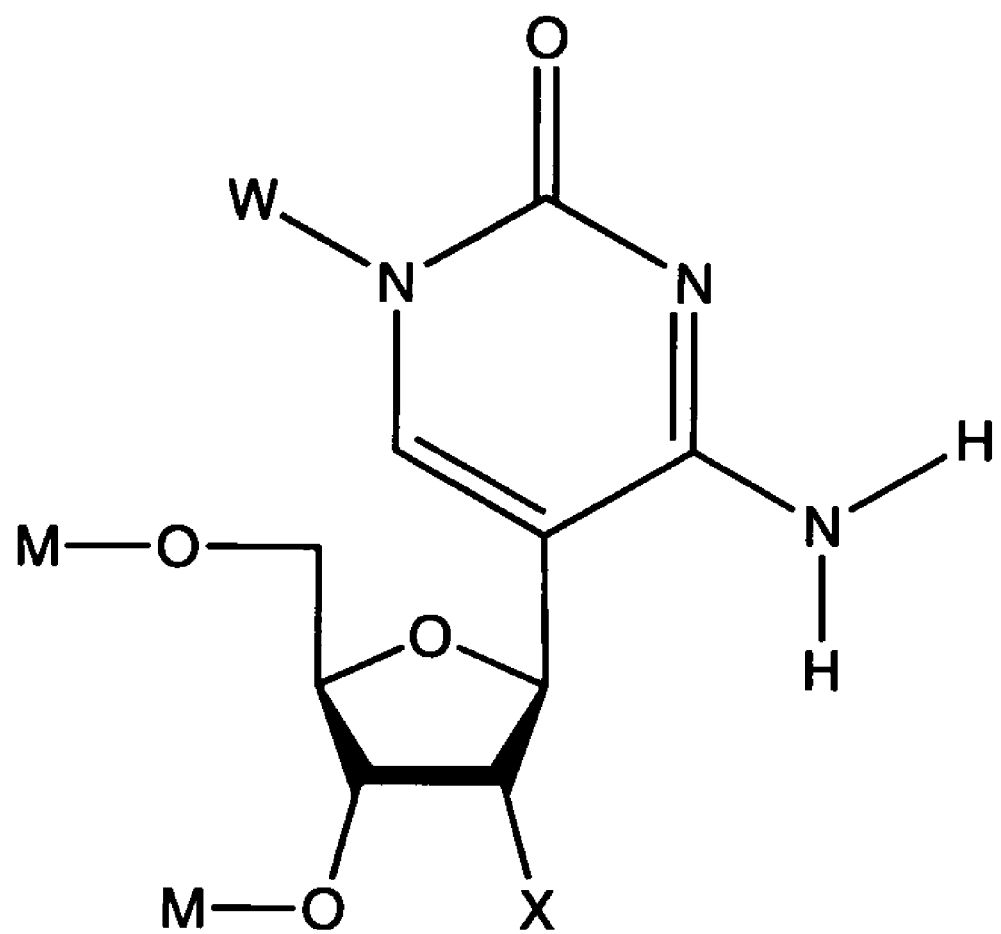
FIG. 3. The general structure of the C-glycoside pyrimidine analog that implements the pyAAD hydrogen bonding pattern. If W is H, then a tautomer exists that is complementary to guanine. This is useful if one expressly desires the conversion of the non-standard nucleobase pair into a C-G base pair, which is useful for cloning and sequencing the derivatives. If, however, the application requires exclusive binding to a puDDA complement, W must be anything except hydrogen.

The specific compound of the instant invention that does this is 4-amino-1-alkyl-5-(1'-beta-D-2'-deoxyribofuranosyl)-2(1H)-pyrimidinone, the structure of which is shown in FIG. 3. This is understood to be applicable on the sugar analogs disclosed in the Background section of this specification.

These compositions of matter do not appear to have been disclosed in the prior art. Therefore, 4-amino-1-alkyl-5-(1'-beta-D-2'-deoxyribofuranosyl)-2(1H)-pyrimidinones appear to be novel as compositions of matter in their own right. Likewise, in no case does a publication from the Inventor's laboratory disclose protected phosphoramidites of, triphosphates of, or oligonucleotide analogs containing the composition of instant invention, or experiments covering the enzymatic incorporation of the nucleoside analog of the instant invention, or any of the applications of said oligonucleotides disclosed here.

One key to the invention of 4-amino-1-alkyl-5-(1'-beta-D-2'-deoxyribofuranosyl)-2(1H)-pyrimidinone is the recognition that the substituents on the nitrogen, W in the claims, should not be hydrogen, if the compound is to complement isoguanosine (or another purine presenting the same hydrogen bonding pattern) exclusively. If W is hydrogen, then a tautomeric form of this nucleoside is possible, where that form is hydrogen bonding and size complementary to standard guanine. This dual hydrogen bonding potential is desirable, if binding exclusive to isoguanosine (or another purine presenting the same hydrogen bonding pattern) is not desired. Then W can be a hydrogen. This has utility, for example, when trying to convert the non-standard nucleobase pair into a standard nucleobase pair, for example, for the purpose of cloning it and sequencing it.

This pyrimidine analog can be incorporated into DNA using either standard chemical synthesis, or by reacting the triphosphate with an appropriate polymerase, with the double mutant of HIV reverse transcriptase described by Sismour et al. [Sismour, A. M., Lutz, S., Park, J.-H., Lutz, M. J., Boyer, P. L., Hughes, S. H., Benner, S. A. (2004) PCR amplification of DNA containing non-standard base pairs by variants of reverse transcriptase from human immunodeficiency virus-1. *Nucl. Acids. Res.* 32, 728-735] being presently preferred, where isoguanosine, or one of the nucleoside analogs presenting the puDDA hydrogen bonding pattern disclosed in this specification, is the templating nucleotide. With the chemical synthesis, the exocyclic amino group must be protected, as is known in the art. The presently preferred protecting groups for this purpose are phenoxyacetyl, benzoyl, and dialkylformamidine.

Also for this purpose, the instant invention provides compositions of matter that implement the puDDA hydrogen bonding pattern (complementary to the pyAAD hydrogen bonding pattern in the analogs disclosed in the previous paragraphs) in forms that have a lower amount of the enol form, and that are internally protected. Also to this end, this specification discloses compositions suitable for incorporation of these into oligonucleotides by chemical synthesis, and by enzymatic synthesis.

The rationales for selecting the puDDA compositions of the instant invention are reviewed here, although not wishing to be bound by theory. Given that the keto forms of pyrimidinones normally dominate over enolic forms, the Inventor viewed the enolic tautomer of disoG as an exception in need of explanation. While not wishing to be bound by theory, the Inventor reasoned that the enol form was present in appreciable concentration in disoG because it restores formal aromaticity to the 5-membered imidazole ring, which must be cross-conjugated in the keto tautomer. It is well known that pyrrole is less "aromatic" than imidazole[8]. This suggested to the Inventor that replacement of the imidazole ring of disoG by a pyrrole ring to give 7-deaza-isoguanine might generate a "purine" analog that would also implement the puDDA hydrogen bonding pattern (like disoG), but with less of the enolic tautomer present at equilibrium.

7-Deaza-isoguanine (C7 isoG) and its 2'-deoxynucleoside analog (dC7 isoG) are both known in the art [Seela, F., Menkhoff, S., Behrendt, S. (1986) *J. Chem. Soc. Perkin Trans. II*, 525-530.] [Kazimierczuk, Z., Mertens, R., Kawczynski, W., Seela, F. (1991) *Helv. Chim. Acta*, 74, 1742-1748] [Seela, F., Muth, H.-P., Kaiser, K., Bourgeois, W., Muehlegger, K., Von der Eltz, H., Batz, H.-G. (2001) U.S. Pat. No. 6,211,158 B1.] The crystal structure of dC7 isoG [Seela, F., Wei, C., Reuter, H., Kastner, G. (1999) *Acta Cryst.*, C55, 1335-1337.] and its base-pairing ability have both been studied [Seela, F., Wei, C. (1997) *Chem. Commun.*, 1869-1870] [Seela, F., Wei, C. (1999) *Helv. Chim. Acta*, 83, 726-745.] [Seela, F., Wei, C., Becher, G., Zulauf, M., Leonard, P. (2000) *Bioorg. Med. Chem. Lett.*, 10, 289-2921. The tautomerism of both C7 isoG and dC7 isoG was undetermined, however.

It had not been demonstrated in the prior art that 7-deazaisoguanine derivatives had tautomeric properties needed to create utility. To do this, the O-methyl-7-deaza-isoguanine derivative 6 was prepared by the procedure of Davoll [Davoll, J. (1960) *J. Chem. Soc.*, 131-138.] Reaction with 1-(alpha)-chloro-3,5-di-O-(p-toluoyl)-2-deoxy-D-ribose [Hoffer, M. (1960) *Chem. Ber.-Recl.*, 93, 2777-2781] gave the 3',5'-di-toluoylprotected 2'-deoxyriboside of 2-methoxy-6-amino-7-deazapurine (3). Thiophenol in ethylene glycol [Aliides, J. W., Martin, N. H., Pitt, C. G., Wall, M. E. (1971) *J. Org. Chem.*, 36, 721-723.] successfully generated the di-O-(p-toluoyl)-2'-deoxy-7-deaza-isoguanosine derivative. This compound was converted to the 2'-deoxynucleoside using NaOMe in MeOH to afford 2, which had spectroscopic properties identical to those reported for this compound by Seela et al. The structure of this compound was further confirmed by treatment with diazomethane, which generated the O-methyl derivative The structure of this derivative was identical in all aspects to that previously known compound. The N-methyl derivative was prepared by protection of the exocyclic amino group as the diisobutylformamidine [Zemlicka, J., Holy, A. (1967) *Collect. Czech. Chem. Commun.*, 32, 3159-3168.] [Froehler, B. C., Matteucci, M. D. (1983) *Nucl. Acids Res.*, 11, 8031-8036.], reaction with $CH_3I$, and immediate deprotection by treatment with methanolic $NH_3$/NaOMe, yielding the N-methylated derivative. N-Methylation at the [1]N position was confirmed by long-range (HMBC) and short-range ($HMQ^{22}$) $^1H$-$^{13}C$ NMR correlation spectroscopy.

The $pK_a$ of the nucleoside analog was determined by spectrophotometric titration (pH 2.8 to 13.7) [Kazimierczuk, Z., Shugar, D. (1974) *Acta Biochim. Pol.*, 21, 455-463.1 at 240-350 nm to give values for $pK_1$ and $pK_2$ as 4.3 (±0.1) and 9.9 (±0.2), respectively. These are comparable to the $pK_a$ values of natural nucleobases, and ensure that the C7 isoG heterocycle is largely uncharged in neutral water.

Four tautomeric forms are worthy of consideration for 7-deaza-isoguanine. Based on literature precedent, as well as precedent in other heterocycles, the imino form was considered to be the least likely [Katritzky, A. R., Lagowski, J. M. (1963) *Adv. Het. Chem.*, 1, 339-437.][Cox, R. H., Bothner-By, A. A. (1968) *J. Phys. Chem.*, 72, 1642-1645] [Cox, R. H., Bothner-By, A. A. (1968) *J. Phys. Chem.*, 72, 1646-1649]. This was confirmed by NMR: the $-NH_2$ group was easily identified in the NMR by integration and $D_2O$ exchange.

The UV spectra of 2'-deoxy-7-deaza-isoguanosine in aqueous solution resembles closely that of the N-methylated derivative, and not the O-methylated derivative. This similarity suggests, but does not prove, that the keto tautomer predominates, following the same logic used by Sepiol et al. to infer that the keto tautomer predominates for isoguanosine.

The multiwavelength analysis described by Dewar and Urch [Dewar, M. J. S., Urch, D. S. (1957) *J. Chem. Soc.*, 345-347] was used to suggest that at most, one additional tautomer was present as a major contributor to the mixture. The procedure of Voegel et al. [Voegel, J. J., von Krosigk, U., Benner, S. A. (1993) *J. Org. Chem.*, 58, 7542-7547.] was then used to estimate a value of the keto:enol tautomers in pure water for dC7 isoG. This procedure exploits the fact that in nonpolar solvents, the UV spectra for both disoG and C7 isoG shift from their form in pure water (which resembles the N-methylated derivatives) to a form that resembles the UV spectra of the O-methylated derivatives. This is interpreted as evidence that the tautomeric equilibrium shifts from one favoring the keto tautomer in pure water to one favoring the enol tautomer in pure dioxane.

To obtain quantitative data, the ratio of the extinction coefficients at two wavelengths ($\lambda$=296 and 255 nm for disoG and $\lambda$=305 and 254 nm for dC7 isoG), chosen to maximize the difference between the keto and enol forms, was chosen as a metric for the tautomeric equilibrium constant in dioxane:water mixtures in varying proportions. This was plotted against the Dimroth $E_T(30)$ value, which provides a measure of the local dielectric constant [Kosower, E. M. (1958) *J. Am. Chem. Soc.*, 80, 3253-3260] [Dimroth, v. K., Reichardt, C., Siepmann, T., Bohlmann, F. (1963) *Liebigs Ann. Chem.*, 661, 1-37.] [Reichardt, C., Harbusch-Goernert, E. (1983) *Liebigs Ann. Chem.*, 721-743] [Gordon, A., Katritzky, A. R. (1968) *Tetrahedron Lett.*, 23, 2767-2770.] [von Jouanne, J., Palmer, D. A., Kelm, H. (1978) *Bull. Chem. Soc. Jpn.*, 51, 463-465].

Even qualitatively, disoG and dC7 isoG behave differently in these experiments. The UV spectrum of disoG changes well before the water is completely removed. In contrast, the UV spectrum of dC7 isoG is not identical to that of the O-methylated derivative even at the highest concentrations of dioxane tested. Further, the UV spectrum of disoG continues to change even in mixtures approaching pure water, this suggests that the conversion of the enolic tautomer to the keto tautomer of disoG is not complete even in pure water (the conclusion of Sepiol et al.). With dC7 isoG, however, the UV spectrum ceases to be solvent dependent when the fraction of water is greater than 50%. These results suggest that our hypothesis at outset had manipulative value: the keto tautomer of dC7 isoG is more stable relative to its enolic tautomer than the keto tautomer of disoG is relative to its enolic tautomer.

The $K_{TAUT}$ (=[keto]/[enol]) for dC7 isoG was then estimated using the method of Voegel et al. Here, the fraction of enol form was estimated over a range of $E_T(30)$ values where the $K_{TAUT}\approx 1$, regions where estimate could be made with some reliability. This is the region where $E_T(30)\approx 40$-50. The log fraction of enol was plotted against $E_T(30)$, and the line was extrapolated to the $E_T(30)$ of pure water (63.1). This generated a value of $K_{TAUT}\approx 10^3$. Recalculating the $K_{TAUT}$ for isoG gave a value of $\approx 10$, consistent with that previously reported. This can be compared with the value for the natural guanosine nucleoside ($K_{TAUT}\approx 10^4$-$10^5$).

The 7-deaza feature of these species has another advantage. Because there is no nitrogen at this center, a valence is free to which substituents cant be attached. Therefore, the invention provides for the synthesis of 7-deazaisoguanosine derivatives that carry substituents at the 7-position. These have additional utility if they carry units including (but not limited to) fluorescent groups, fluorescent quenchers, catalytically useful functionality, capture tags, and conformationally constraining units.

Figure 4:
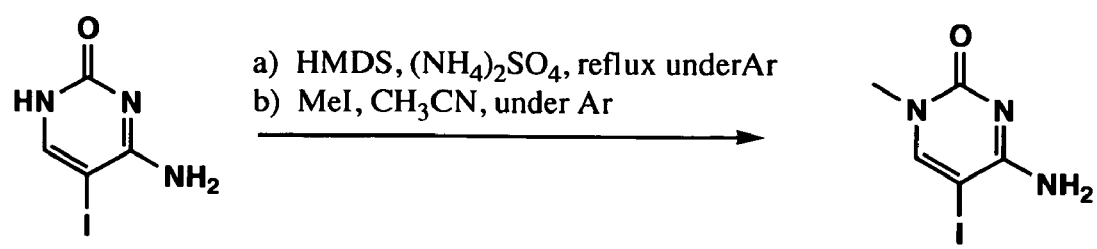
FIG. 4. The process for adding a simple alkyl substituents (W=methyl) to iodocytosine. Other electrophiles may be used to introduce other W groups.

These substituents provide another opportunity, as they can form a third ring. This does not change the hydrogen bonding pattern of the nucleoside analog as it is presented on the Watson-Crick edge of the nucleobase. It does, however, change the hydrogen bonding properties of the nucleoside in the major groove. Isoguanosine itself makes strong interactions in the major groove. These can be disadvantageous. Thus, structures of the type shown in FIG. 4 are therefore disclosed as those that avoid this interaction.

These purine analogs can be incorporated into DNA using either standard chemical synthesis, or by reacting the triphosphate with an appropriate polymerase, with the double mutant of HIV reverse transcriptase described by Sismour et al. [Sismour, A. M., Lutz, S., Park, J.-H., Lutz, M. J., Boyer, P. L., Hughes, S. H., Benner, S. A. (2004) PCR amplification of DNA containing non-standard base pairs by variants of reverse transcriptase from human immunodeficiency virus-1. *Nucl. Acids. Res.* 32, 728-735] being presently preferred, where isocytidine, or one of the nucleoside analogs presenting the pyAAD hydrogen bonding pattern disclosed in this specification, is the templating nucleotide. With the chemical synthesis, the exocyclic amino group must be protected, as is known in the art. The presently preferred protecting groups for this purpose are phenoxyacetyl, benzoyl, and dialkylformamidine. In addition, it is presently preferred to also protect the exocyclic oxygen of the nucleobase, preferably as the p-nitrophenylethyl (NPE) ether.

EXAMPLES

Example 1

Synthesis of the C-glycoside Implementing the pyAAD Hydrogen Bonding Pattern

The pyAAD analog is prepared by coupling the appropriate iodinated heterocycle with an unsaturated sugar using the Heck strategy [Zhang, H. C., Daves, G. D. Jr. (1992) *J. Org. Chem.* 57, 4690], or a Pd catalyst that has a different ligand (such as the bis(benzylideneacetone) ligand system). Following the Pd coupling, subsequent deprotection and reduction of the exposed 3'-keto group results in the generation of the desired nucleoside. This heterocycle is cytidine, which is iodinated by treating with N-iodosuccinimide in DMF at room temperature.

The synthesis of the sugar is based on the work of Larson et al. [Larsen, E., Jorgensen, P. T., Sofan, M. A., Pedersen, E. B. (1994) *Synthesis,* 1037 and Cameron et al. [Cameron, M. A., Cush, S. B., Hammer, R. P. (1997) *J. Org. Chem.* 62, 9065]. Starting with thymidine, the 5'-hydroxyl group is first protected as a p-Tol ester. The 3'-hydroxyl group is then protected as the 3'-tert-butyldiphenylsilyl ether. Deprotection of this species with methanolic ammonia produces the monoprotected thymidine precursor. Treatment with hexamethyldisilazane in the presence of ammonium sulfate under reflux gives the diprotected sugar, which on stirring with powdered potassium carbonate in methanol liberated the desired carbohydrate, ready for palladium coupling.

For the compositions of the instant invention, cases, the cytidine N-1 nitrogen must be alkylated, as this removes any tautomeric ambiguity in the corresponding nucleosides. This is known in the literature, and is achieved in a sequence that begins by treatment with HMDS, and continues with treatment with an alkylating agent. This allows the incorporation of a wide range of substituents, W in the claims. Since polymerases tolerate large substitutents at this position, a variety of groups can be appended at this position, including the fluorescent tags, the fluorescence quenchers, the metal chelating agents, and other species mentioned in the Background section.

Figure 6:
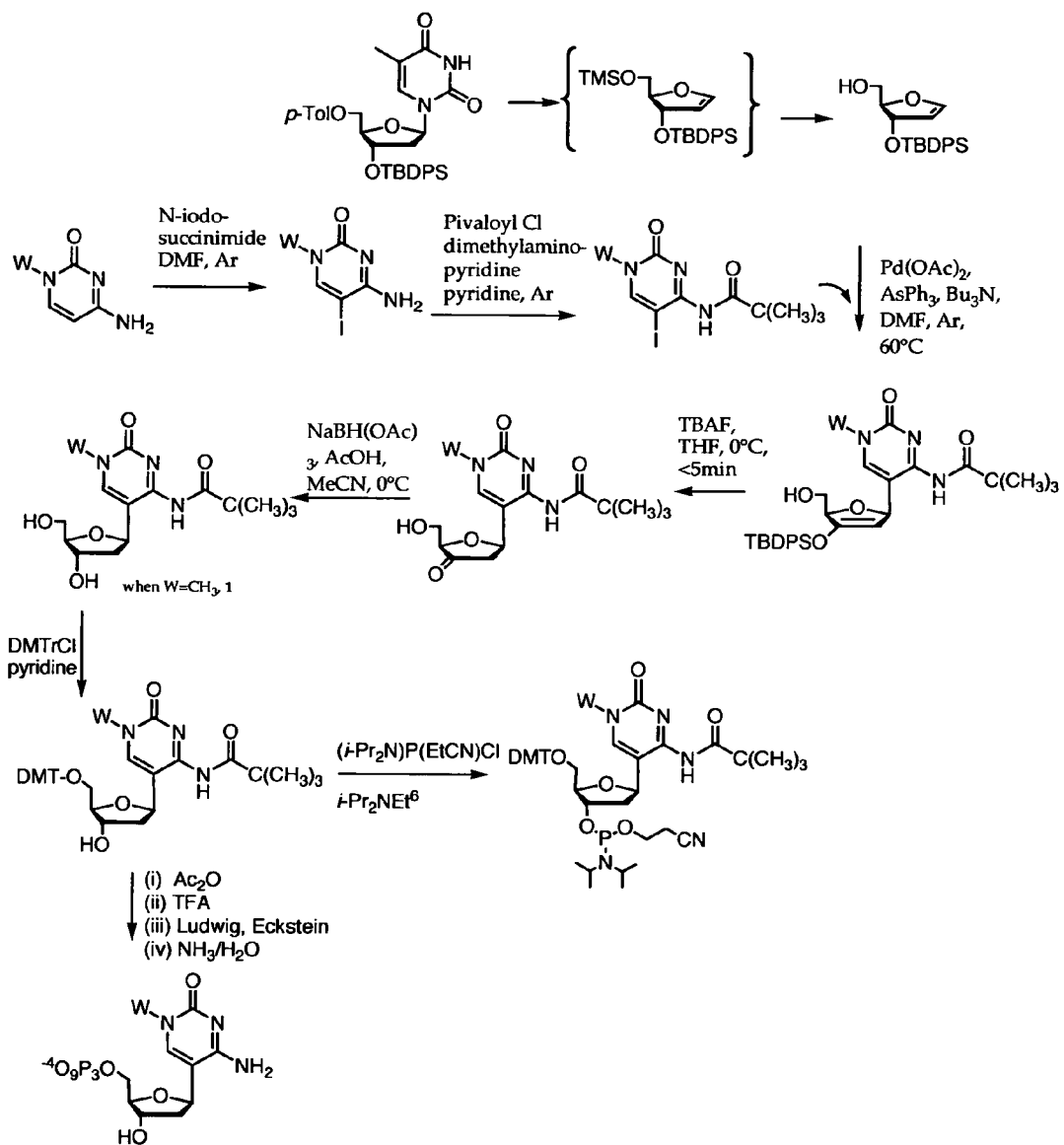
FIG. 6. Synthesis of the glycal, an intermediate in the synthesis of the compositions of the instant invention, and the coupling of this to give a protected pyAAD analog suitable for incorporation into oligonucleotides using standard triphosphate synthesis, and conversion to a triphosphate. Analogous procedures are used for the puDDA analogs of the instant invention. These protecting groups can be carried on to the nucleoside analog.
Figure 7:
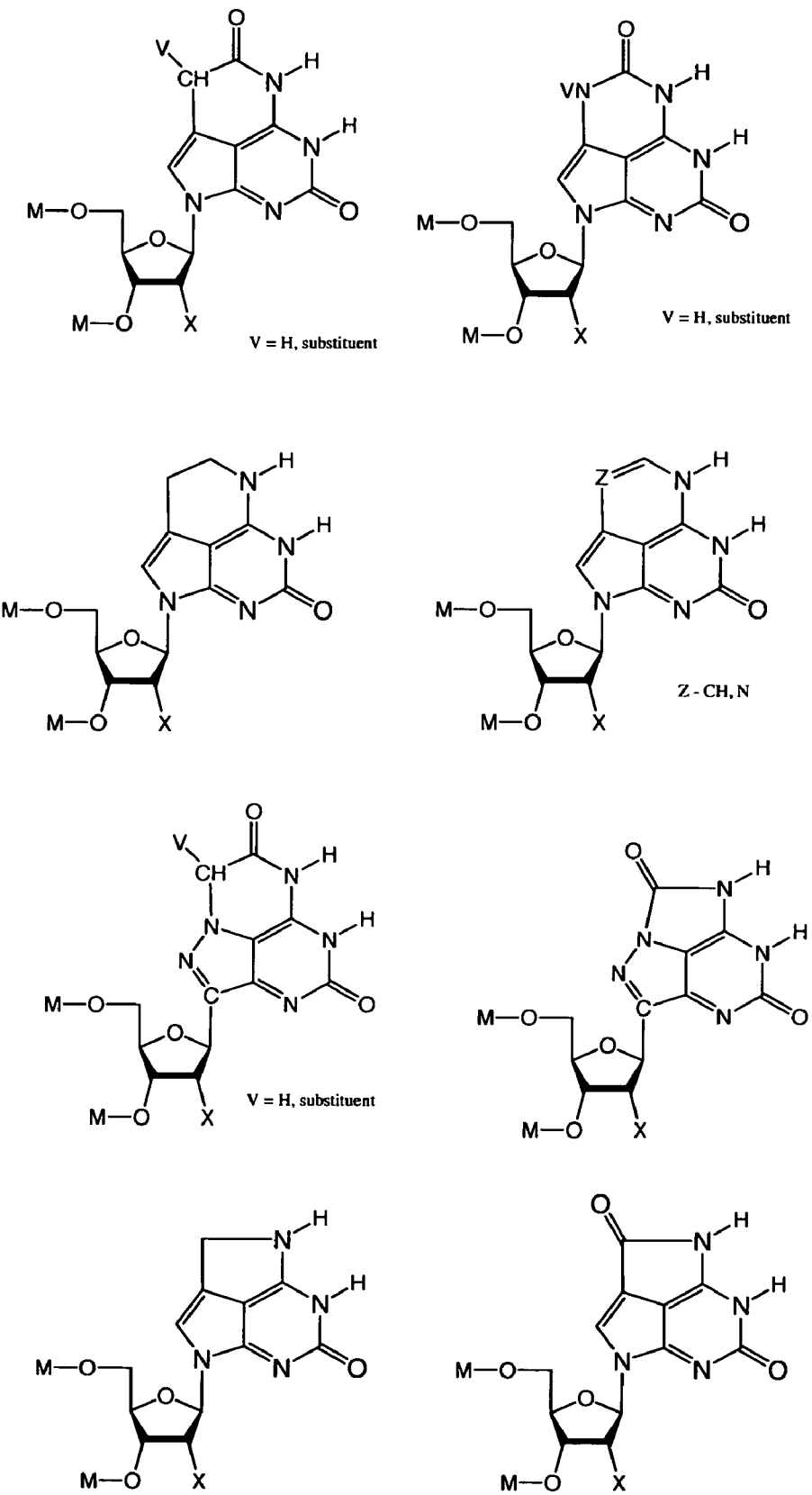
FIG. 7. Cyclic derivatives implementing the puDDA hydrogen bonding pattern.
Figure 8:
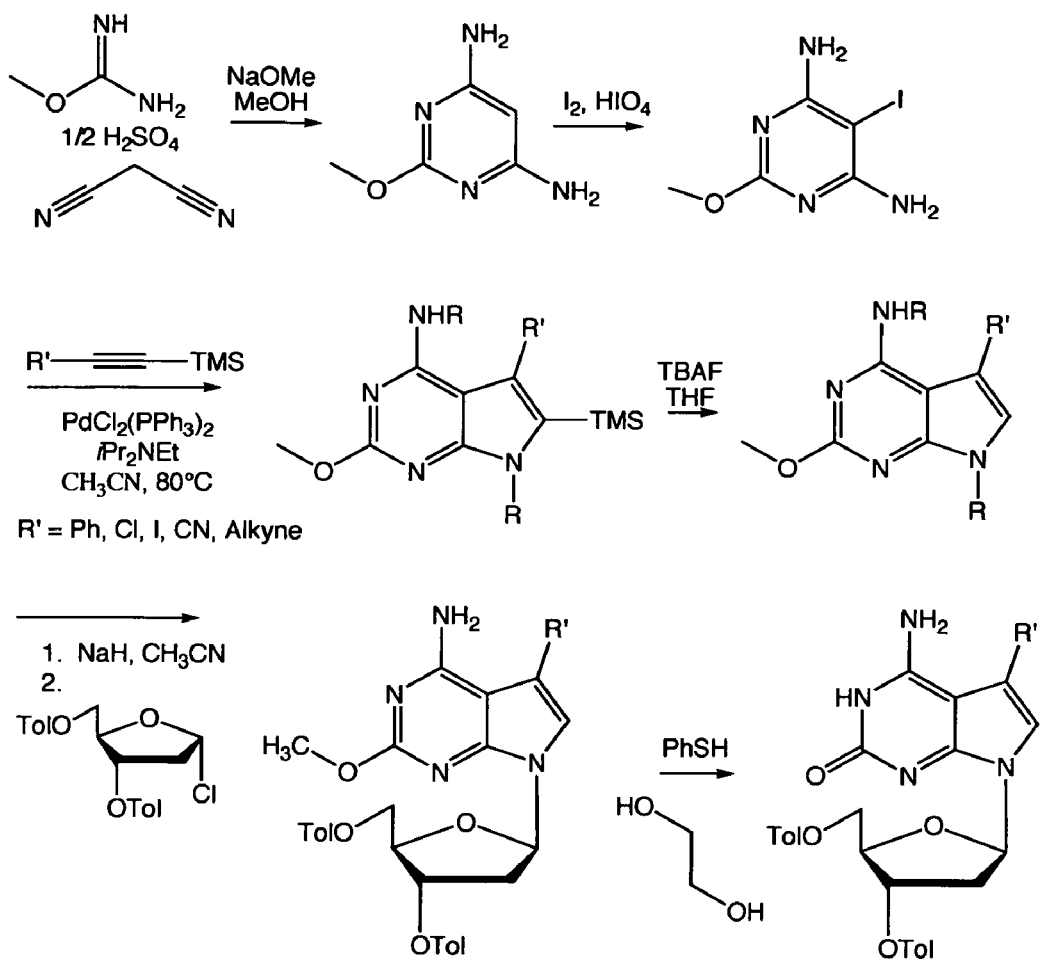
FIG. 8. Schematic showing the synthesis of 7-deazaisoguanine as the 2'-deoxyriboside. Analogous routes readily apparent to one of ordinary skill in the art provide access to the riboside, and the various derivatives, including the triphosphate and protected phosphoramidites. R' is variable, and includes, without limitation, the indicated R's.
Figure 9:
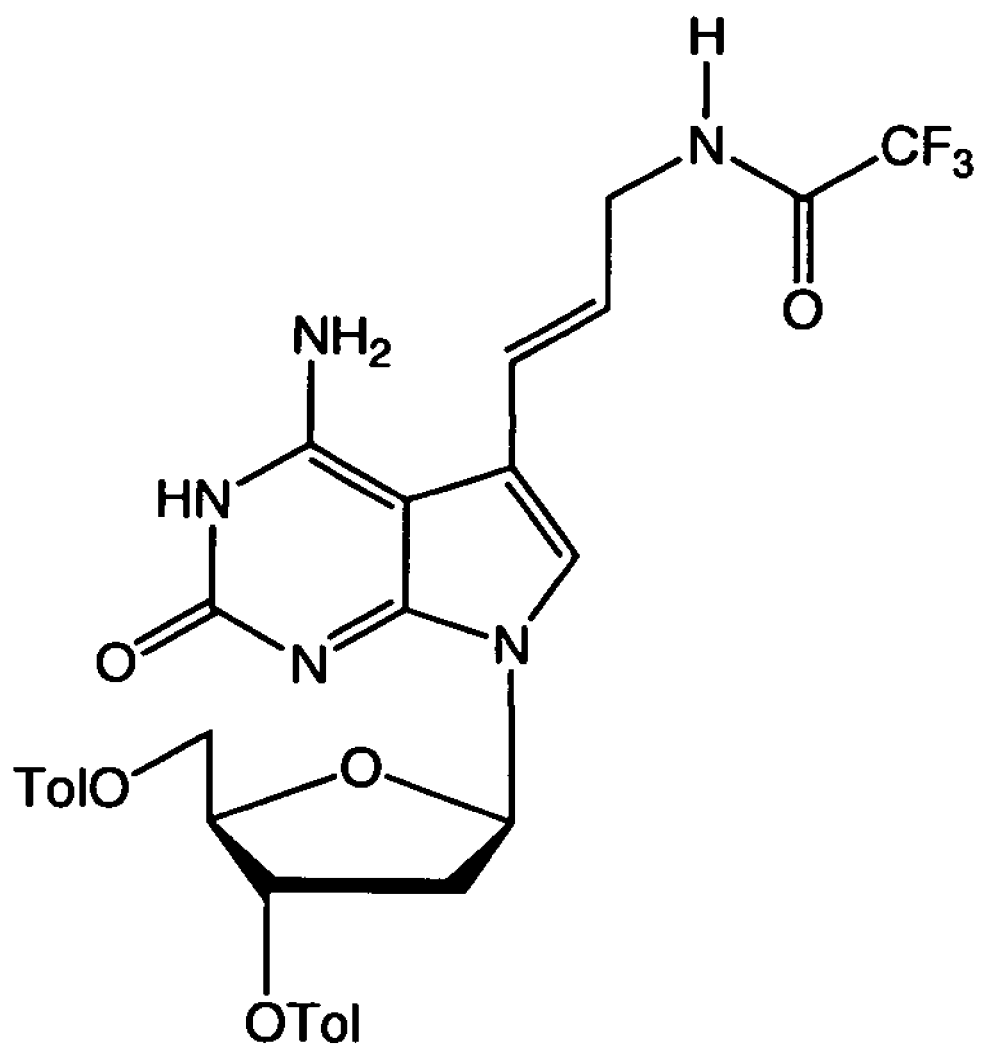
FIG. 9. The product when the trifluoracetamide-alkene-alkyne is used in the scheme in FIG. 8
Figure 10:
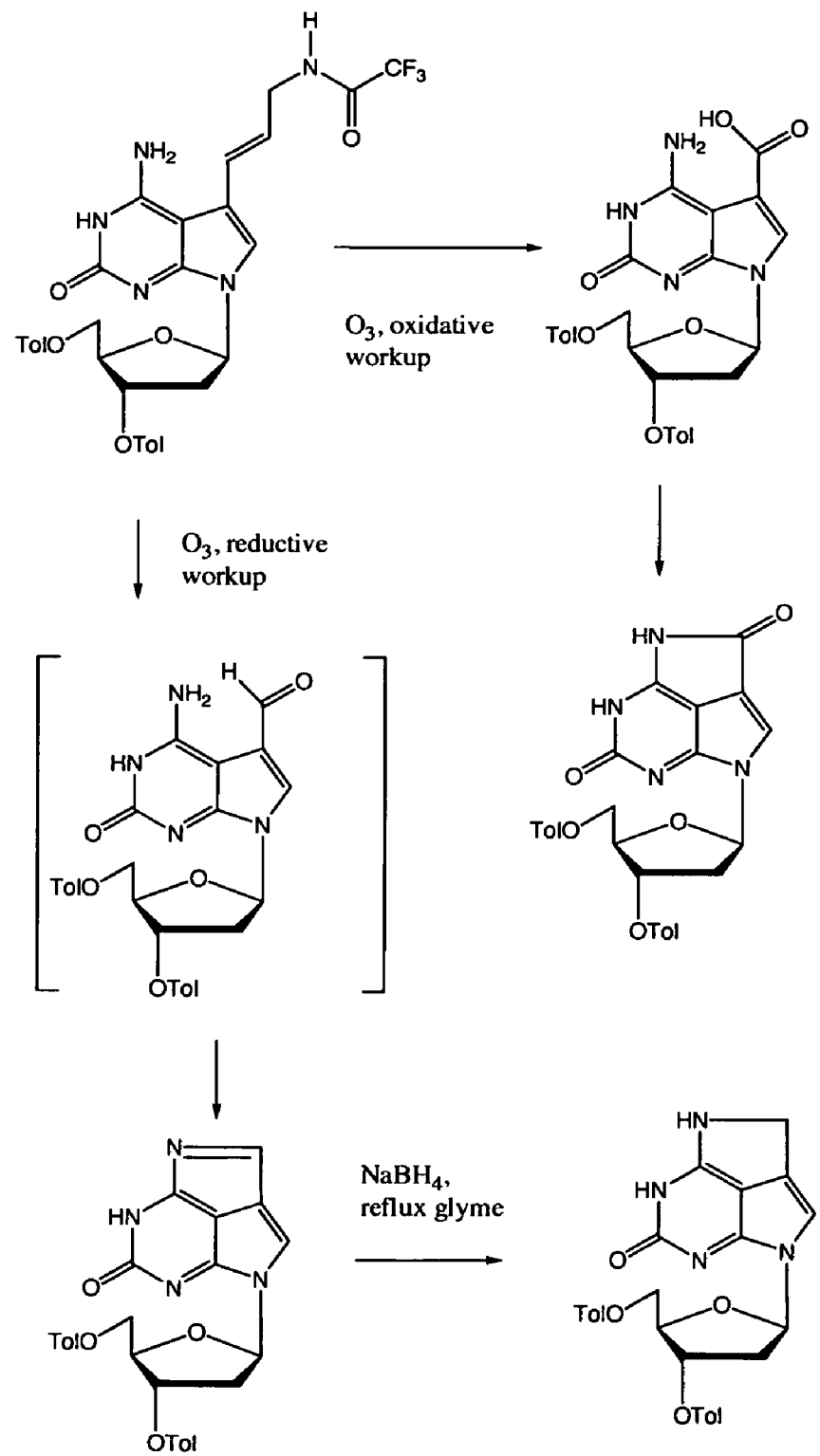
FIG. 10. Conversion of the product in FIG. 9 to cyclic derivatives shown in FIG. 7.
Figure 11:
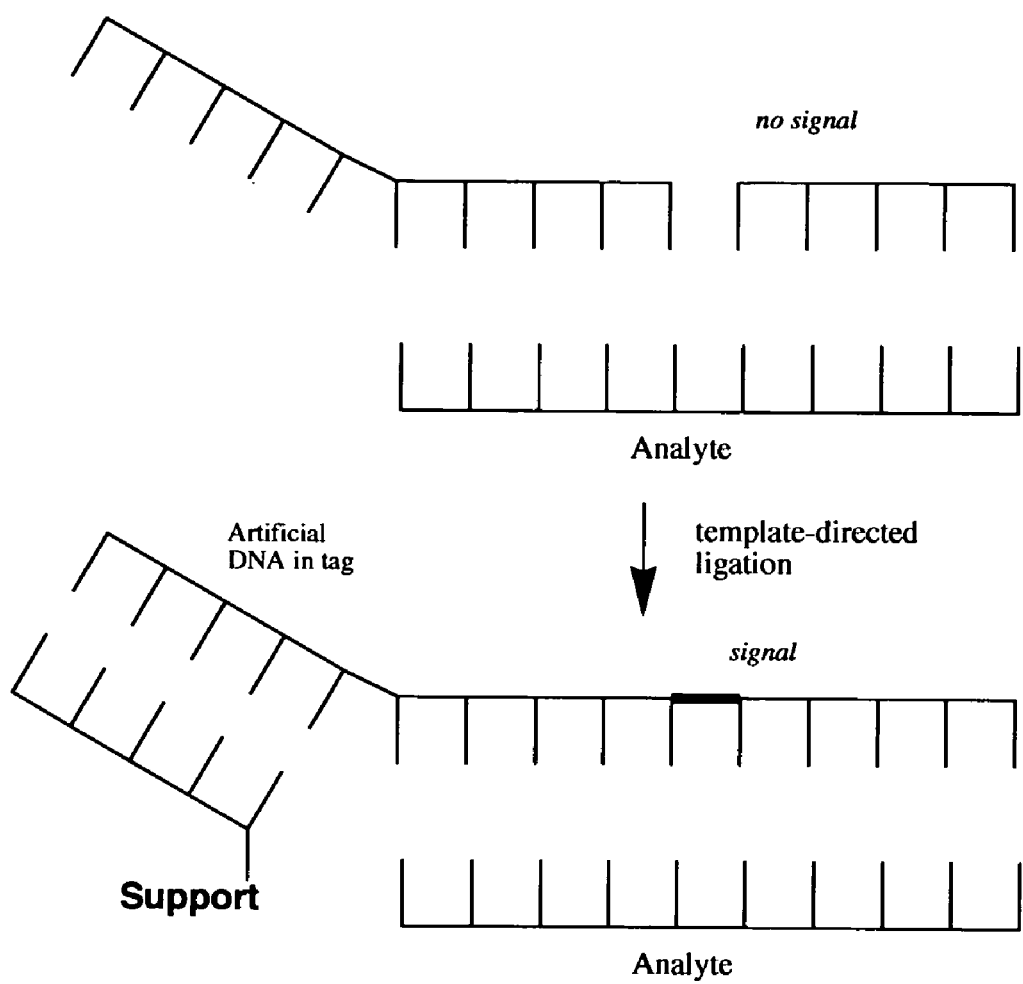
FIG. 11. An architecture using the oligonucleotide analogs of the instant invention in tags in a detection scheme. The architecture illustrates the process of binding two oligonucleotide analogs of the instant invention.
Figure 12:
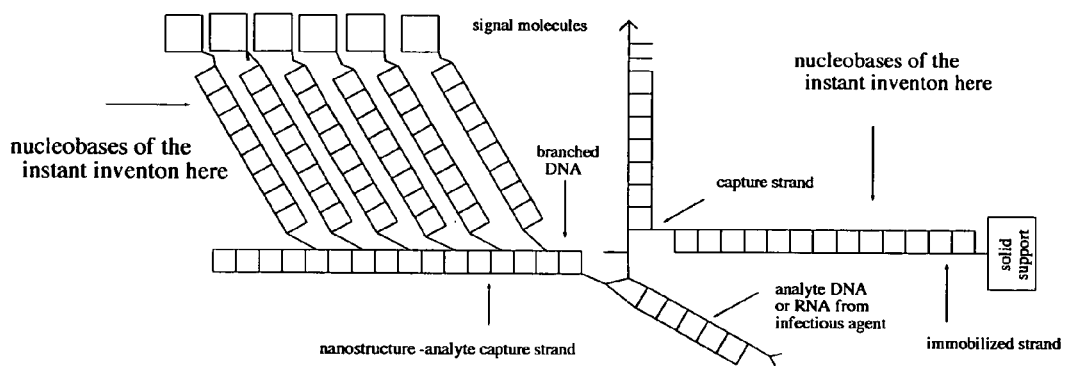
FIG. 12. An architecture using the oligonucleotide analogs of the instant invention as part of a dendrimeric signal maplification structure.
Figure 13:
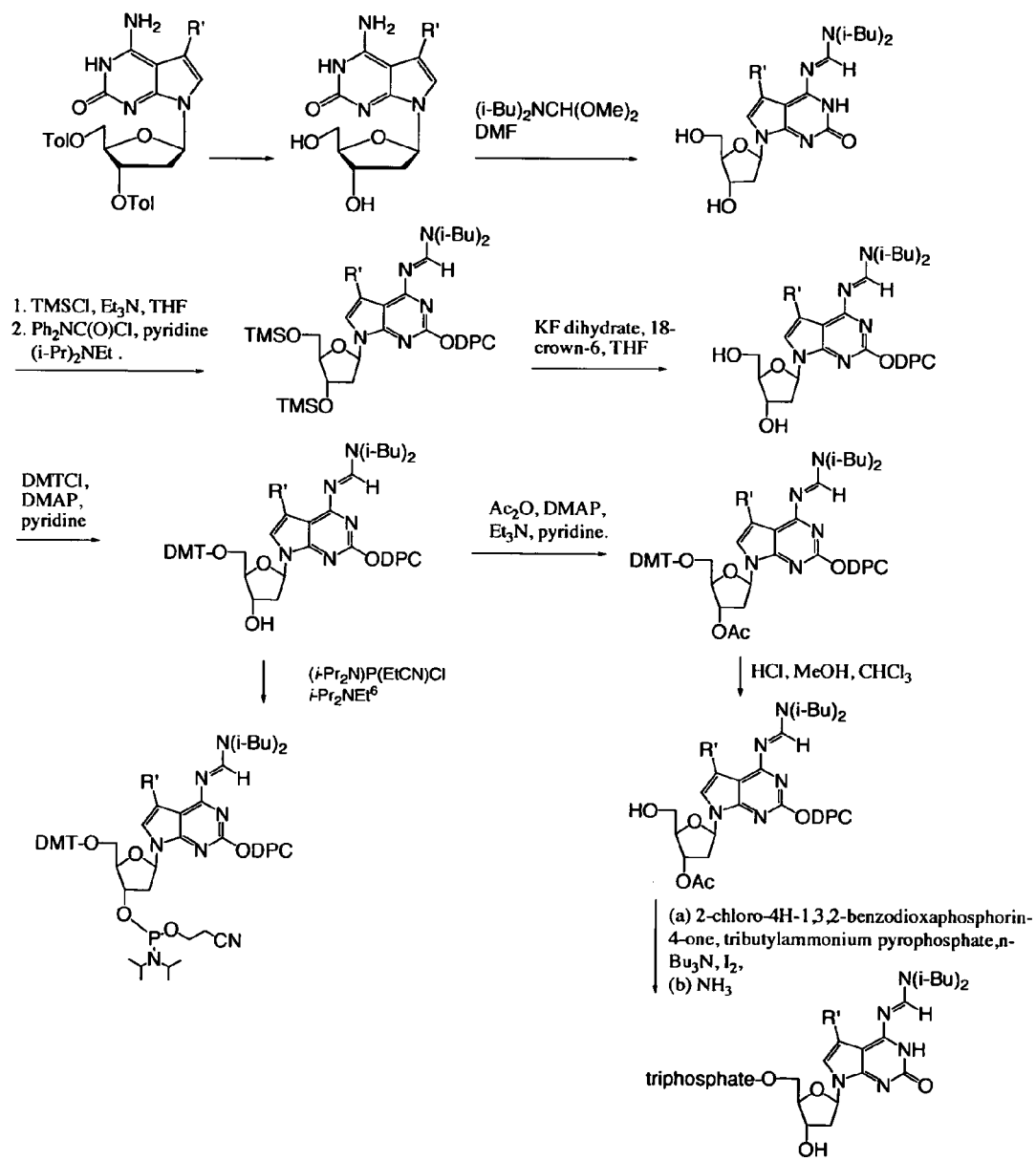
FIG. 13. Synthesis of protected isoguanosine derivatives suitable for oligonucleotide synthesis.

Protection of the exocyclic amino group is desired for the preparation of precursors for oligonucleotide analog synthesis and the preparation of triphosphates and other derivatives. Easily removable protecting groups (for example, the phenoxyacetyl group) is preferred for triphosphate synthesis, and for oligonucleotide synthesis that includes delicate units in the product. The strategies for protection are outlined in FIG. 6.

Transformations following the synthesis of the nucleoside analog, including preparation of protected phosphoramidites suitable for solid phase synthesis, synthesis of oligonucleotide analogs containing the nucleobase analog of the instant invention, preparation of the triphosphates, preparation of immobilized derivatives, preparation of tagged derivatives, and preparation of other compounds as disclosed in the examples, follows routes well known in the art.

5'-p-Tol-thymidine p-Toluoyl chloride (6.78 mL, 51.25 mmol) is added dropwise (to keep the temperature of the reaction mixture below 5° C.) to a stirred suspension of thymidine (12.112 g, 50 mmol) in anhydrous pyridine (50 mL) under an Ar atmosphere and cooled on an ice/water bath. After addition is complete, the bath is removed and the mixture is allowed to warm to room temperature. After 16.5 h, TLC (EtOAc) showed that no starting material remained. The mixture is poured into ice (50 g), and after the ice melts, the white precipitate is collected by filtration (ca. 12.8 g). The aqueous filtrate is extracted with $CH_2Cl_2$ (3×50 mL) and the combined organic extracts were washed with 1M HCl (3×50 mL), sat $NaHCO_3$ (3×50 mL) and water (3×50 mL). The $CH_2Cl_2$ solution is dried ($MgSO_4$), filtered and the filtrate concentrated under reduced pressure to give a pale yellow foam (3.00 g). The solid material is combined, and recrystallized in ca. 2 g batches from $CH_2Cl_2$ (300 mL). After each filtration, the volume of the filtrate is reduced to 100 mL and cooled, a white solid crystallizing from solution is collected by filtration. This filtrate is used as the solvent for the next crystallization. This is done multiple times. The insoluble solids which had been removed after each crystallization are combined and recrystallized as above.

3'-TBDPS-5'-Tol-thymidine

TBDPSCl (0.26 mL, 1.1 mmol) is added to a stirred solution of 5'-Tol-thymidine (0.360 g, 1.0 mmol) and imidazole (0.218 g, 3.2 mmol) in DMF (5 mL) under an atmosphere of Ar. The reaction is stirred at RT for 48 h. If TLC (2:1 EtOAc: hexanes) shows that unreacted starting material remains, additional TBDPSCl (0.26 mL, 1.1 mmol) is added, and stirring is continued an additional 24 h. Concentration under vacuum without heat gives an oil, which is taken up in $CH_2Cl_2$ (10 mL) and washed with 1M HCl (3×10 mL), sat $NaHCO_3$ (3×10 mL), water (3×10 mL), dried ($MgSO_4$), filtered and the filtrate concentrated under reduced pressure to give crude 3'-TBDPS-5'-Tol-thymidine (0.923 g) as a pale yellow gum.

3'-TBDPS-thymidine

A saturated solution of methanolic ammonia is added to crude 3'-TBDPS-5'-Tol-thymidine (0.923 g). The reaction vessel is sealed with a septum and the reaction mixture is stirred at 40° C. for 2 days. The solvent is removed under reduced pressure to give crude 3'-TBDPS-thymidine (0.931 g) as a pale yellow oil.

3-TBDPS-5-TMS-glycal

HMDS (5 mL) is added to crude 3'-TBDPS-thymidine (0.931 g) and powdered ammonium sulfate (0.025 g, 0.19 mmol) which is under an atmosphere of argon. The reaction mixture is stirred and heated under reflux for 3 h. The reaction mixture is then removed from the heat, and after it had cooled to room temperature, the solvent is removed under reduced pressure (high vacuum pump) without the use of a heat source. The resulting gum is taken up in cyclohexane (10 mL), washed with sat. $NaHCO_3$ solution (3×10 mL), dried ($MgSO_4$), filtered, and the filtrate concentrated under reduced pressure to give crude 3-TBDPS-5-TMS-glycal (1.003 g) as a yellow oil.

3-TBDPS-glycal

Powdered potassium carbonate (0.152 g, 1.1 mmol) is added to a solution of crude 3-TBDPS-5-TMS-glycal (1.003 g) in methanol (10 mL). The reaction is stopped after 10 min via addition of HOAc (0.126 mL, 2.2 mmol). The residual solid is filtered off, and the filtrate concentrated under reduced pressure. The resulting orange oil is taken up in $CH_2Cl_2$ (10 mL), washed with water (3×10 mL), dried with $MgSO_4$, filtered, and the filtrate concentrated under reduced pressure to give crude 3-TBDPS-glycal as a pale yellow oil. Purification by flash chromatography (1:5 EtOAc:hexanes) gave pure 3-TBDPS-glycal (as a colorless oil.

Iodination

DMF (50 mL) is added to a mixture of cytosine (8.333 g, 75 mmol) with N-iodosuccinimide (18.562 g, 82.5 mmol) under Ar. The vessel is covered in foil and ultrasonicated for 30 min to disrupt the solid mass at the bottom of the vessel. The mixture is then stirred for an additional 12 h, the still heterogeneous reaction mixture is added to water (150 mL). The insoluble material is collected by filtration, washed with water and dried over $P_2O_5$ to give the iodinated heterocycle is a pale tan solid (17.703 g, 99%). The material is used without further purification.

5-Iodo-1-methyl-isocytosine

HMDS (20 mL) is added to a mixture of the iodinated heterocycle from above (3.555 g, 15 mmol) with powdered ammonium sulfate (0.075 g) under Ar. The reaction mixture is stirred and heated to reflux for 6.5 h. After this time, the mixture is removed from the heat, allowed to cool, and the solvents removed under vacuum to give a dark brown oil. The oil is dissolved in acetonitrile (20 mL). Methyl iodide (9.34 mL, 150 mmol) is then added under Ar. The mixture is stirred for 1 day, the crude product is collected by filtration. Crystallization from water and decolorizing with charcoal gave the product a pale yellow crystalline solid. More material is obtained by concentrating the filtrate.

Pivaloyl Protection

Pivaloyl chloride (15.8 mL, 128.3 mmol) is added in one lot to a stirred mixture of the iodinated methylcytosine derivative from above (2.008 g, 8 mmol) and DMAP (1.955 g, 16 mmol) in anhydrous pyridine (32 mL) under Ar. The mixture is stirred for 18 h. Triethylamine (16 mL) is then added, and the vessel is cooled in an ice/water bath. Ethanol (32 mL) is slowly added to the mixture. The mixture is concentrated under reduced pressure, and the resulting solid is partitioned between dichloromethane (50 mL) and water (50 mL). After removing the aqueous phase, the organic solution is washed with water (2×50 mL), dried ($MgSO_4$), filtered, and the filtrate concentrated under reduced pressure to give crude material. Purification by flash chromatography (1:3 ethyl acetate: hexanes) gave the desired material as a pale yellow solid (1.943 g, 72%).

Analogous procedures protect the exocyclic amino group as the PAC derivative.

Pd Coupling of the Glycal to the Iodinated Heterocycle

DMF (20 mL) is added to a mixture of palladium acetate (0.099 g, 0.44 mmol) and triphenyl arsine (0.339 g, 1.11 mmol) under an Ar atmosphere. The reaction mixture is stirred, and the initially clear yellow solution became cloudy. After 20 min, a solution of the iodoheterocycle (1.854 g, 5.53 mmol), glycal (2.354 g, 6.64 mmol) and tri-n-butylamine (2.04 mL, 8.58 mmol) in DMF (10 mL) (prepared in a different flask under an Ar atmosphere) is added by syringe in one portion. This flask is washed with additional DMF (2×5 mL), and the washings also added to the reaction mixture, which is now a clear orange solution. The reaction mixture is heated to 60° C. After 3 days, TLC (1:3 ethyl acetate:hexanes) showed that there is no starting material remaining. The reaction mixture is removed from the heat, allowed to cool, and the solvent removed under reduced pressure (high vacuum pump) without the use of a heat source. The resulting dark brown oil is dissolved in methanol, adsorbed onto silica, and purified by flash chromatography (2:5 ethyl acetate:hexanes) to give an impure sample of the desired product, as well as some dehalogenated heterocycle. This material is dissolved in a small volume of 1:3 ethyl acetate:hexanes. The desired product crystallized from solution as a white solid. The filtrate is concentrated under reduced pressure to dryness, and this is repeated to give an additional crop of material. The filtrate is again concentrated under reduced pressure to dryness and the solid dissolved in a small amount of 1:5 ethyl acetate:hexanes, which gave more material. This filtrate is concentrated to dryness, and purified by flash chromatography (1:3 ethyl acetate:hexanes) to give more of the desired product.

Deprotection

A solution of TBAF in THF (3.00 mL, 1.0 M, 3.00 mmol) is added to a solution of the coupled product (1.124 g, 2.00 mmol) in THF (4 mL), cooled in an ice/water bath under an Ar atmosphere. The reaction mixture immediately became yellow, and after 1 min TLC (1:1 ethyl acetate:hexanes) showed that there is no starting material remaining. The reaction is quenched by addition of methanol (2 mL) and the reaction mixture is concentrated under reduced pressure. The resulting yellow oil is purified twice by flash chromatography (3:1 ethyl acetate:hexanes) to give the desired product as a pale yellow foam.

Reduction of the Ketone

Sodium triacetoxyborohydride (0.549 g, 2.475 mmol) is added in one lot to a solution of the hydroxy ketone (0.534 g, 1.65 mmol) in acetonitrile (8 mL) and acetic acid (4 mL) under an Ar atmosphere. TLC (ethyl acetate) indicated that there is no starting material after 12 min. The reaction is quenched by the addition of acetone, and the reaction mixture concentrated under reduced pressure. The resulting pale yellow gum is dissolved in methanol, adsorbed onto silica, and purified by flash chromatography (ethyl acetate) to give the desired material as a white solid.

Tritylation of the Derivative

The protected nucleoside analog (8.7 mmol) is dissolved in dry pyridine (150 mL). To the solution is added 4',4''-dimethoxytrityl chloride (1.2 equiv). The reaction mixture is stirred at room temperature for 24 hours. The reaction is quenched by the addition of water (3 mL). The solution is concentrated under vacuum, and an aqueous solution of $NaHCO_3$ (80 ml) is added. The mixture is extracted with EtOAc, dried ($Na_2SO_4$), the solvents evaporated under reduced pressure, and the product isolated by column chromatography (chloroform/acetone 9:1, then 9:2).

Phosphoramidite.

The protected derivative from above (0.12 mmol) is dissolved in $CH_3CN$ (2.0 mL). The solution is then treated with bis-(N,N-diisopropylamino)-3-cyanoethyloxyphosphine (Aldrich, 1.2 equiv.), and diisopropylammonium tetrazolide (0.06 mmol), following a literature procedure] McBride, L. J., Kierzek, R., Beaucage, S. L. & Caruthers, M. H. (1986) *J. Am. Chem. Soc.* 108, 2040-2048]. The progress of the reaction is monitored by TLC ($SiO_2$ eluted with EtOAc:$CH_2Cl_2$:triethylamine 45:45:10). An additional portion (0.02 mL) of bis-(N,N-diisopropylamino)-3-cyanoethyloxyphosphine is then added, and stirring continued for an additional hour. Water (2 drops) is added, the mixture stirred for 15 min, the mixture diluted with $CH_2Cl_2$ (30 mL), and the organic layer washed with aqueous $Na_2CO_3$ (2%) and dried ($Na_2SO_4$). The phosphoramidite is isolated by chromatography ($SiO_2$, EtOAc:$CH_2Cl_2$:triethylamine 45:45:10 as eluant). $^{31}$P-NMR 149.7 (doublet of diastereomers).

Example 2

Synthesis of the Triphosphate of the Analog Implementing the pyAAD Hydrogen Bonding Pattern 3'-O-(Acetyl) Derivative of the Nucleoside Analog The dimethoxytritylated nucleoside analog from above (0.200 mmol) is coevaporated with dry pyridine (0.8 mL). The residue is redissolved in pyridine (1 mL) under dry Ar. Acetic acid anhydride (10 equiv) is added dropwise, and the reaction mixture is stirred for 3 h. The solution is then cooled on an ice bath, and the reaction is quenched by addition of methanol (1 mL). The solvents are evaporated under reduced pressure. The remaining foam is coevaporated with dry toluene (1 mL), and the residue is dissolved in a mixture of trifluoroacetic acid and $CH_2Cl_2$ (2% v/v, 10 mL total volume). The mixture is then stirred for 30 min, at which point saturated aqueous $NaHCO_3$ solution (5 mL) is added. The phases are separated, the aqueous phase isolated, and the aqueous phase extracted with $CH_2Cl_2$. The combined organic phases are concentrated under reduced pressure, and the remaining yellowish oil is resolved by chromatography on silica gel ($CH_2Cl_2$/MeOH 98:2) to afford the 3'-O-acetyl derivative of the nucleoside, with its 5'-OH group free.

5'-O-Triphosphate Derivative of the Nucleoside Analog

The 3'-acetylated nucleoside analog (0.162 mmol) is then coevaporated again with dry pyridine (1 mL). The residue is then redissolved in a mixture of dry pyridine (162 µL) and dry 1,4-dioxane (486 µL) under Ar. A freshly prepared solution of 2-chloro-4H-1,3,2-benzodioxaphosphorin-4-one (1 M) in 1,4-dioxane (1624, 1.0 equiv) is then added to the stirred reaction mixture. A white precipitate forms immediately. After 10 minutes, a well vortexed emulsion of tributylammonium pyrophosphate (110 mg) in DMF/tri-n-butylamine (3:1, 648 µL) is quickly added. This causes the precipitate to dissolve immediately. After 10 minutes of incubation at room temperature, a 1% solution of iodine in pyridine/water (98:2, 3.24 mL) is added dropwise. After 15 min following completed addition of the iodine solution, the solvents are removed at 40° C. under reduced pressure. The remaining brown oil is dissolved in water/MeOH (1:1, 10 mL), and the mixture is allowed to stand for 30 minutes. Then, a portion of solution of aqueous concentrated ammonia (20 mL) is added, the solution turns turbid. The suspension is stirred for 1 h, the solvents are removed at 40° C. under reduced pressure, and the remaining light brown oil is coevaporated with water. Water/acetonitrile (95:5, 2 mL) is then added to yield a light brown suspension. The unsoluble components are removed by filtration (0.2µ cellulose acetate membrane) to yield a clear, slightly yellow, filtrate containing the triphosphate. The triphosphate is purified by chromatography (DEAE Sephadex, 30 mL, 1.5×18 cm, TEAB 0.1 M to 0.8 M (linear gradient) in the presence of 10% acetonitrile). Further purification is done by reversed phase RP-HPLC (Column: Nova-Pak HR C18 cartridge (Waters), 6µ, 25×100 mm. Solvent A: triethylammonium acetate (25 mM, pH 7.0), solvent B: acetonitrile. Flow rate: 5.5 mL/min. Gradient: 0-1 min 100% A, 10 min 13% B (linear), 55 min 18% B (linear)). The eluate is lyophilized to dryness, and the residue is redissolved in water. Dissolution and lyophilization is done three more times, to remove the residual triethylamonnium acetate. The triphosphate is stored at −20° C., either as 5 mM solution in water or as a lyophilized powder. The triphosphate can be recognized by characteristic signals in the $^{31}$P NMR in $D_2O$ solvent (121 MHz: δ relative to phosphoric acid=−7.9 (poorly resolved doublet), −9.1 (doublet), and −20.6 (triplet) ppm).

Example 3

Synthesis of Functionalized Derivatives of the pyAAD Analog

The heterocyclic system carrying a acid side chain other than methyl is obtained by adding alternative electrophiles, including acrolein and ethyl acrylate. These provide carboxylate functionalities that can be converted to tagged species following procedures well known in the art.

Example 4

Chemical Synthesis of Oligonucleotide Analogs Incorporating the pyAAD Analog

Oligonucleotide analogs containing non-standard nucleotide are prepared by "trityl off" solid-phase synthesis using an Applied Biosystems automated DNA synthesizer from the β-cyanoethyl protected phosphoramidites. They are purified by polyacrylamide gel electrophoresis (12-20%). Chemicals are from Glen Research, while the DNA membrane columns (0.2 μmol scale) and CPG columns (1.0 μmol scale) containing the 3'-terminal nucleoside are from PerSeptive Biosystems.

Vials to contain the protected phosphoramidite of the nucleoside analog are rinsed with acetone and immediately placed into an oven at 150° C. to dry overnight. The vials are then cooled to room temperature in a dessicator over $P_2O_5$ under vacuum of <1 ton. The dessicator is vented with dry Ar, and phosphoramidite is placed into the vials. If only a small amount of phosphoramidite is available, the compound is transferred into the prepared vial as solution in $CH_2Cl_2$, and the solvent is evaporated under reduced pressure. Subsequently, the vials containing the phosphoramidites are returned to the desiccator with $P_2O_5$ to be stored under vacuum. The desiccator is vented with dry Ar, and the vials are immediately closed and stored in a dessicator containing anhydrous $MgSO_4$ until needed.

Directly before oligonucleotide synthesis, the phosphoramidites are dissolved in anhydrous acetonitrile (0.15 g/1.5 mL). Standard phosphoramidites are used as solutions in anhydrous acetonitrile (0.5 g/10 mL) at half the concentration that is recommended by the synthesizer manufacturer. Synthesis on a 0.2-1.0 μmol scale is performed using a standard synthesis protocol, with the exception of an extended coupling time (600 s) for the analog.

After the synthesis is complete (0.2-1.0 μmol scale), the column material (CPG beads) is transferred into a 1.5 mL microcentrifuge tube with sealed screw cap. Upon addition of conc. $NH_4OH$ solution (1 mL), the tube is shaken in an Eppendorf shaker at maximum speed overnight at 55° C. After the mixture had been centrifuged for a few seconds, the supernatant is transferred into a clean microfuge tube. The column material is washed with water (250 μL), and the supernatant is combined with the first supernatant. The solvent is evaporated from the combined supernatants by means of a speed vac at ambient temperature. The residue is dissolved in NaOAc solution (0.7 M, pH 5.2, 300 μL). An occasionally occurring cloudy precipitation is removed by filtration through a syringe filter with cellulose acetate membrane (pore size 0.2 μm). Ice cold EtOH (1 mL) is added to the clear solution. After vortexing, the mixture is stored at −20° C. for several hours. The mixture is then centrifuged at 4° C. and 14,000 rpm for 30 min, and the supernatant is removed. The remaining pellet is washed with 80% aqueous EtOH (1 mL) by gentle shaking, and the mixture is centrifuged again at 4° C. and 14,000 rpm for 10 min. After removal of the supernatant, the oligonucleotide pellet is dried by exposure to the air and redissolved in water (500 μL).

The oligonucleotide analog is purified by either HPLC that is obtained after above described post synthetic processing is mixed with PAGE loading buffer (1:1). The mixture is incubated at 95° C. for 2 min and immediately loaded onto the preheated polyacrylamide gel. Up to ¼ of a 0.2 μmol synthesis or 1/20 of a 1.0 μmol synthesis is loaded into one well. Electrophoresis is performed at 45-55 W, maintaining a gel temperature of 55-60° C. When the desired oligonucleotides had migrated ca. 25 cm as judged by the dye markers, electrophoresis is stopped. The oligonucleotide bands are visualized by UV quenching with the help of a silica gel coated TLC plate containing a fluorescence indicator. The desired bands are cut out with a razor blade. Usually the slowest migrating band of a crude mixture corresponded to the desired full length product. The gel pieces are transferred into tubes of appropriate size and crushed with the help of a pipette tip. NaOAc solution (300 mM, pH 7.5) is added to completely cover the gel particles. The mixture is shaken vehemently on a vortexer for 5 h to overnight. After centrifugation, the supernatant is removed. The gel particles are shaken with a fresh portion of NaOAc solution (300 mM, pH 7.5) for a few hours. The supernatant is filtered and combined with the supernatant from the first extraction. The combined supernatants are filtered through a cellulose acetate membrane (pore size 0.2 μm). The oligonucleotide is recovered from the filtrate by EtOH precipitation. The pellet is washed with 70% EtOH. The so obtained oligonucleotides are pure enough for all subsequent applications. They are stored as solutions in water (3-250 pmol/μL) at −20° C.

The concentrations of the oligonucleotide solutions are determined via measurement of the UV absorbance of the oligonucleotide solution at λ=260 nm.

The relation between UV absorbance and the amount of the oligonucleotide (in nanomoles) present in the sample is given approximately by the formula $A_{260}*100/n$=nmole oligonucleotide, where $A_{260}$ is the absorbance at λ=260 nm in OD, and n is the number of bases of the oligonucleotide. This formula is employed for both standard and functionalized oligonucleotides without consideration of the extinction coefficient of the functionalized bases.

Oligonucleotide analogs are analyzed by anion exchange HPLC under the following conditions:

Column: Dionex

Solvent A: Sodium phosphate (20 mM, pH 6.0), solvent B: Sodium phosphate (20 mM, pH 6.0), NaCl (1 M), solvent C: ACN.

Gradient: 0-1 min 75% A/25% C, 30 min 55% B/25% C (linear).

For purification of large amounts of oligonucleotides (up to 10 OD), a larger column with the same packing material is used. The gradients are adjusted to keep the $R_t$ value about constant. On the preparative scale, the oligonucleotides are further purified and desalted on a larger column (Nova-Pak HR® C18 cartridge (Waters), 6 μm 60 Å, 25×100 mm, flow rate 5.5 mL/min). Chromatography times are extended by 5 min.

Oligonucleotide analogs containing the nucleotide analog are characterized by MALDI-TOF mass spectrometry. Short oligonucleotides (9-10mers) are in addition analyzed by electrospray ionization mass spectrometry (ESI MS). The oligonucleotide is injected as solution in isopropanol/water (1:1) containing TEA (30 mM).

The oligonucleotide analogs can be further analyzed by enzymatic degradation. The analog is dissolved in water/acetonitril mixtures (9:1, 4.0 μL). Digestion buffer (0.1 M Tris-HCl, pH 8.3, 20 mM $MgCl_2$, 4.0 μL) and 10 mM $Zn(OAc)_2$ solution (1.0 μL) is then added, followed by phosphodiesterase I (1.0 μL, 0.0006 U), nuclease P1 (1 μL, 0.0006 U) and alkaline phosphatase, diluted with digestion buffer (1.0 μL, 1.5 U). The mixture is incubated at 50° C. for 5 h. The sample is then diluted with triethylammonium acetate buffer (1 M, pH 7.0, 20 μL) and water/acetonitrile (9:1, 70 μL), filtered and analyzed using RP-HPLC (Column: Adsorbosphere, Solvent A: TEAOAc (25 mM, pH 7.0), solvent B: solvenacetonitrile 4:1, solvent C: acetonitrile. The composition of the oligonucleotide is verified by using the integrated absorbance of the component nucleosides at 260 nm In this fashion, the following oligonucleotides are prepared:

A Molecular Beacon Containing the Disclosed Nucleoside Analog and its Complement in the Stem,
SEQ ID 4 Fl-5'-<u>YTYYR</u>TGTGTTTTCTACAAGCTGAT<u>GYRRAR</u>-3'-Qu Y represents the pyAAD nucleoside analog incorporated into a DNA strand. R represents the large complement to Y that presents a hydrogen bond donor-donor-acceptor pattern, which are part of the instant invention. A, T, G, and C represent the 2'-deoxyribonucleotides as generally disclosed in the literature. Fl is a fluorescent moiety, in this example rhodamine. Qu is a fluorescence quencher moiety, here DABCYL.

An Oligonucleotide Analog Suitable for Immobilization Using Avidin Analogs.
SEQ ID 2 5'-biotin-<u>YTYYR</u>TGTGTTTTCTACAAGCTGATG where Y represents a pyAAD nucleoside analog 1 incorporated into a DNA strand. R represents the puDDA complement. A, T, G, and C represent the 2'-deoxyribonucleotides as generally disclosed in the literature. Fl is a fluorescent moiety. Qu is a fluorescence quencher moiety. This is able to mediate the capture of the following oligonucleotide to a solid support, which may be a two dimensional array, a one dimensional array, or a bead:
SEQ ID 1 3'-<u>RARRY</u>ACACAAAAGATGTTCGACTACAAAAAAGA where R, Y, and ATCG are defined as above. The process of the capture is performed at room temperature in phosphate buffer (0.1 mM, pH 7.0) in the presence of NaCl (500 mM).

A Primer-Template Combination.
SEQ ID 2 5'-YTYYRTGTGTTTTCTACAAGCTGATG-3' (primer)
SEQ ID 3 3'-<u>ACACAAAAGATGTTCGACTACAAAAR</u>YGACTTGTACAT-5'(template)
where R, Y, and ATCG are defined as above.

Example 5

Enzymic Synthesis of Oligonucleotide Analogs Containing the Disclosed Nucleoside Analog Under the Direction of a Template Primer Extension Experiments.
In a typical primer extension experiment, 5'-$^{32}$P-labeled primer having the sequence shown below:
SEQ ID 2 5'-YTYYRTGTGTTTTCTACAAGCTGATG-3' (primer)
SEQ ID 3 3'-<u>ACACAAAAGATGTTCGACTACAAAAR</u>YGACTTGTACAT-5'(template)
where Y represents the pyAAD nucleoside analog incorporated into a DNA strand, R represents the puDDA complement, and A, T, G, and C represent the 2'-deoxyribonucleotides as generally disclosed in the literature.

The template, in this example, has the sequence shown above (656 nM of the primers, 920 nM of the templates). The reaction is run in the buffer appropriate for the polymerase or reverse transcriptase supplier (sold by the polymerase or reverse transcriptase supplier). Here, the preferred polymerase is double mutant of HIV reverse transcriptase disclosed by Sismour et al. [op. cit.] from New England Biolabs. The components are mixed with dATP, dGTP, dCTP, TTP and dQTP (Q is the nucleoside analog, either R or Y, all triphosphates at a final concentration 130 µM each) in a total volume of 160 µL. After heating the mixture to 95° C. for 1 min, the primer/template complex is annealed by cooling slowly to room temperature over 1 h. Primer extension is started by addition of the polymerase (16 µL). The mixture is then incubated at the optimal temperature for the polymerase. Aliquots (25 µL), taken at various times during the elongation reaction, are quenched by addition of a premixed solution of sodium acetate (2.5 µL, 3 M, pH 5.2), EDTA (1 µL, 0.5 M, pH 8), and ethanol (50 µL). After being stored at −20° C. for 20 min, the samples are centrifuged (14,000 rpm, 4° C., 20 min) and the pellets dried in the vacuum concentrator. The residues are redissolved in PAGE loading buffer and the samples separated on a 10% PAGE gel (7 M urea). The gel is analyzed using the MolecularImager®. To improve reproducibility in cases where multiple reactions are run in parallel, a master mixture of primer/template and the dNTPs is prepared by scaling up the listed procedure. Master mixtures are not stored for more than 24 hours at −20° C.

Standing Start Experiments.
The primer (15 pmol, 5'-$^{32}$P-labeled) and template (21 pmol) are incubated with polymerase at the conditions specified by the supplier, with the volume adjusted with water to 21 µL with water. The DNA is denatured (95° C., 1 min) and cooled to room temperature over a period of 1 hour. After addition of the appropriate dNTPs (1.67 µL, 130 µM final concentration of each) and an aliquot of Taq polymerase (0.2 U), the mixture is incubated for up to 30 min at 37° C. The reaction is quenched by addition of a premixed solution of sodium acetate (2.5 µL, 3 M, pH 5.2), EDTA (1 µL, 0.5 M, pH 8), and EtOH (50 µL), the DNA is recovered by centrifugation, and the pellet is dried in the vacuum concentrator. The DNA is dissolved in PAGE loading buffer (bromophenol blue/xylene cyanol mix 0.1 g, water, 1 mL, and formamide, 4 mL) and analyzed using a 10% PAGE gel (7 M urea). The gel is analyzed with the MolecularImager®.

Example 6

Enzymic Synthesis of a Library of Random Sequence Oligonucleotide Analogs Containing the Non-Standard Nucleotide Using Terminal Transferase, not Under the Direction of a Template In a 1.5-ml Eppendorf-tube is added:

| | |
|---|---|
| 1. Water | 642.0 µL |
| 2. Cacodylate buffer (5x conc.) | 200.0 µL |
| 3. MgCl$_2$ (100 mM) | 80.0 µL |
| 4. CoCl$_2$ (100 mM) | 40.0 µL |
| 5. dNTP-Mix (each 10 mM dATP, dCTP, dGTP, TTP, and dQTP) | 25.0 µL |

The final concentration is each triphosphate is 0.25 mM, the are total 1 mM triphosphate.

| | |
|---|---|
| 6. Seq1 (20) (113 pmol/µL, = total 1 nmol) | 8.9 µL |
| 7. Terminal transferase (25 units/µL, = total 100 units) | 4.0 µL |

The sodium cacodriate-trihydrate buffer is prepared by dissolving (2.14 g, 10 mmol) in ca. 5 ml of water. Tris•HCl buffer (1.25 mL, 1.0 M, pH 8.0), 1.25 mL acetylated bovine serum albumin (10 mg/ml, New England Biolabs) and water are mixed to a final volume of 10 mL. The pH is adjusted at 6.6 by adding a few drops of concentrated HCl and the stock solution sterilized by ultrafiltration. The mixture is stored at −20° C.

Prior to the reaction mixture is shaken briefly and incubated for 16 hours at 37° C. In the beginning the solution is clear, a white precipitate is observed to form, presumably cobalt pyrophosphate. To stop the reaction, the tube is placed on ice and diluted with 0.1 volume of an EDTA solution (200 mM in water, pH=8). The reaction mixture is divided into four Eppendorf tubes and the DNA is precipitated with ethanol (addition of 0.11 volumes of 3.0 M NaOAc, pH=5.4 and 2.5 volumes of ethanol. The mixture is stored at −20° C. overnight, centrifuged at 4° C. for 30 min, the supernatant is removed by pipette and discarded. The precipitate is washed with 500 µl of 70% ethanol, dried for 2 hours in air at RT, and dissolved in 100 µl water to yield a solution of ≦1 nmol DNA "Seq 1-random" (21) in 400 µl water.

The DNA oligos are analyzed by agarose gel electrophoresis (2% agarose in TAE-buffer, ethidium bromide) using pBR 322 MspI-digestion as markers. The sample consisted of 5.0 µl DNA-solution (≦1 nmol 21 in 400 µl water) plus 1.0 µl gel loading buffer III (6× conc.). The gel is developed (30 min, 76 V), and visualized under ultraviolet light (l=254 nm). The gel of the mixture of oligodeoxyribonucleotides 21 displayed (as expected) no sharp bands, but rather a "smeared" band with a center at ca. 300 nt, and visibly extending from 200 to 600 nt.

Example 7

Synthesis of 7-deazaisoguanosine Derivatives Having a Side Chain Appended

Nucleosides bearing the parent 7-deazaisoguanosine have been prepared by Seela. The synthesis below provides routes to 7-deazaisoguanosine derivatives that carry substituents at the 7-position. These will have utility if they carry units including (but not limited to) fluorescent groups, fluorescent quenchers, catalytically useful functionality, capture tags, and conformationally constraining units, and others described in the Background section. The Dissertation of Theodore Martinot (University of Florida, 2004) is cited. A procedure for preparing one set of derivatives, and the cyclized forms, is described here.

N-(3-Chloro-allyl)-2,2,2-trifluoro-acetamide

Trifluoroacetamide (10.44 g, 92.4 mmol) is dissolved in THF (30 mL). Sodium hydride (60% weight dispersion in mineral oil, 3.1 g, 77 mmol) is then added in small portions at room temperature while regulating the temperature of the reaction with a water bath. The mixture is stirred at room temperature for 5 min., after which E-1,3-dichloropropene (4.5 mL, 49.4 mmol) is added. After 2 min., the mixture thickened, and the reaction was heated to reflux for 45 min. The mixture is then cooled to room temperature, and saturated aqueous ammonium chloride (20 mL) and water (40 mL) are added. The mixture is transferred to a separatory funnel and extracted with ether (2×400 mL). The combined organic layers were dried (MgSO$_4$) and concentrated under reduced pressure to obtained a colorless oil that was used for the next step.

N-(3-Chloro-allyl)-2,2,2-trifluoro-acetamide

Trifluoroacetamide (10.44 g, 92.4 mmol) is dissolved in THF (30 mL). Sodium hydride (60% weight dispersion in mineral oil, 3.1 g, 77 mmol) is then added in small portions at room temperature while regulating the temperature of the reaction with a water bath. The mixture is stirred at room temperature for 5 min., after which E-1,3-dichloropropene (4.5 mL, 49.4 mmol) is added. After 2 min., the mixture thickened, and the reaction was heated to reflux for 45 min. The mixture is then cooled to room temperature, and saturated aqueous ammonium chloride (20 mL) and water (40 mL) are added. The mixture is transferred to a separatory funnel and extracted with ether (2×400 mL). The combined organic layers were dried (MgSO$_4$) and concentrated under reduced pressure to obtained a colorless oil that was used for the next step.

2,2,2-Trifluoro-N-(5-trimethylsilanyl-pent-2-en-4-ynyl)-acetamide

N-(3-Chloroallyl)-2,2,2-trifluoro-acetamide (863 mg, 4.62 mmol) is dissolved in piperidine (3 mL), and dichlorobis(triphenylphosphine)palladium (131 mg, 0.19 mmol), and copper(I) iodide (60 mg, 0.32 mmol) are added under nitrogen. After 2 min., the solution turns light green, and TMS-acetylene (1 mL) is then added. The solution is allowed to stir overnight at RT under nitrogen, after which mixture is dark red. The reaction mixture is concentrated under reduced pressure, loaded onto a silica gel column, and purified using flash column chromatography with methylene chloride as the solvent to give the product as a colorless oil. R$_f$ 0.5 (80:20—hexanes:ethyl acetate)

5-Iodo-2-methoxy-pyrimidine-4,6-diamine

O-Methylisourea hemisulfate (14.35 g, 117 mmol) is dissolved in methanolic sodium methoxide (1 M, 117 mL, 117 mmol). Malononitrile (7.73 g, 117 mmol) is added. The mixture is heated to reflux for 3 hours and monitored by TLC. Analytical samples of the pyrimidine product are obtained by flash column chromatography using gradients of methylene chloride and methanol. Otherwise, the material is not purified. Instead, the mixture is allowed to cool. Then, iodine (22.33 g, 88 mmol) is added, and the mixture is allowed to stir at room temperature for 2 hours. Upon complete consumption of the intermediate pyrimidine, ethyl ether (500 mL) is added and the solution is transferred to a separatory funnel. Aqueous HCl (1 M, 300 mL) is then added, and the organic and aqueous layers are separated. The aqueous layer is retained and washed with ethyl ether (2×300 mL). The pH is adjusted to 8 by adding NaOH pellets, and the mixture is extracted with ethyl acetate (3×300 mL). The organic phase is dried (MgSO$_4$) and concentrated under reduced pressure to give product that is recrystallized from toluene or hexanes.

Tricyclic 7-deazaguanosine derivatives

Figure 5:
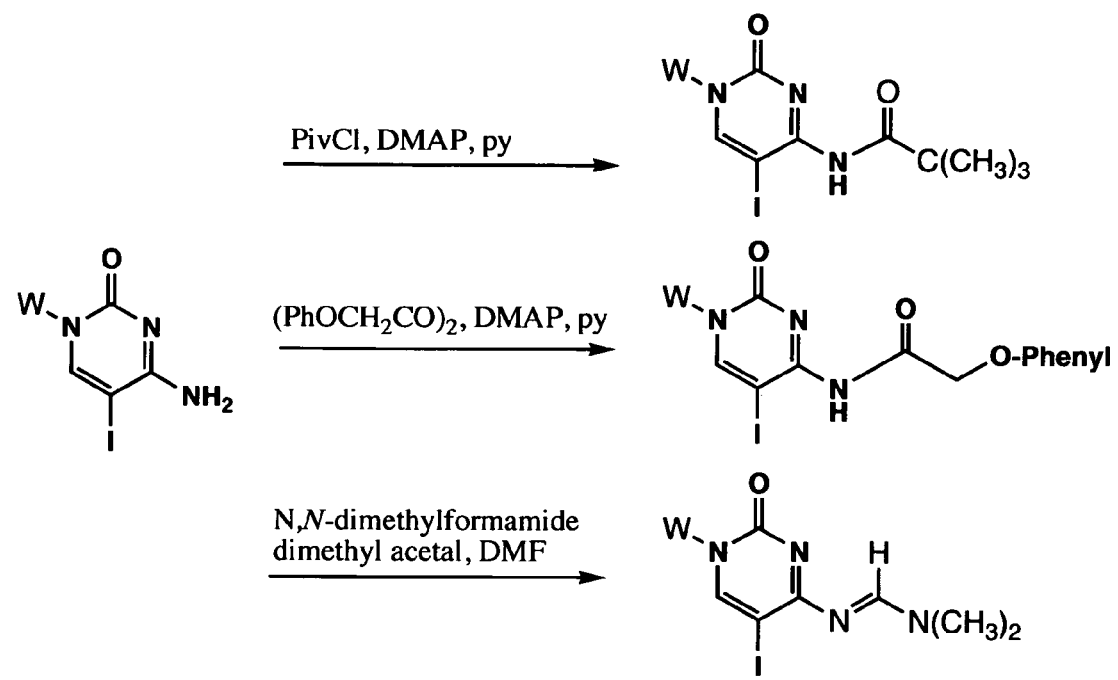
FIG. 5. Synthesis of protected precursors for the pyAAD implementation of the instant invention.

The 5-iodo-2-methoxy-pyrimidine-4,6-diamine (3 g, 11 mmol) is dissolved in acetonitrile (50 mL). Then, a trimethylsilylacetylene carrying the desired functionality (11 mmol0 is added with dichlorobis(triphenylphosphine)palladium (0.45 mmol), and Huenigs base (65 mmol). The mixture is heated at reflux for 3 hours. At this time, TLC shows complete loss of the starting pyrimidine. The mixture is concentrated under reduced pressure and purified using flash column chromatography to yield the product as an off-white solid. This generates the generic 7-deazaisoguanine precursor having the exocyclic oxygen protected as a methyl ether, an R'-group appended to C-7, and a TMS substituents on carbon 8. The last is removed by treatment with TBAF in THF to give the heterocycle, where R (FIG. 5) is H. This is coupled to a chloro-2'-deoxyriboside in protected form, following procedures known in the literature. The methyl group is removed in ethyleneglycol with thiophenol, to generate the functionalized 7-deazaisoguanosine derivative.

N-[3-(4-Amino-2-methoxy-6-trimethylsilanyl-7H-pyrrolo[2,3-d]pyrimidin-5-yl-allyl]-2,2,2-trifluoroacetamide When the acetylene is the 2,2,2-trifluoro-N-(5-trimethylsilanyl-pent-2-en-4-ynyl)-acetamide from above, the product of this reaction is N-[3-(4-amino-2-methoxy-6-trimethylsilanyl-7H-pyrrolo[2,3-d]pyrimidin-5-yl)-allyl]-2,2,2-trifluoro-acetamide. 5-Iodo-2-methoxy-pyrimidine-4,6-diamine (3.27 g, 12.3 mmol) is dissolved in acetonitrile (50 mL). 2,2,2-Trifluoro-N-(5-trimethylsilanyl-pent-2-en-4-ynyl)-acetamide (3.209 g, 12.87 mmol), dichlorobis(triphenylphosphine)palladium (0.328 g, 0.467 mmol), and Huenig's base (12 mL, 69 mmol) are added. The mixture is heated to reflux for 3 hours. The mixture is concentrated under reduced pressure to yield product, which is purified using flash column chromatography. The silyl group is removed with tetrabutylammonium fluoride in THF at room temperature.

Tricyclic 7-deazaguanosine derivatives from N-[3-(4-amino-2-methoxy-6-trimethylsilanyl-7H-pyrrolo[2,3-d]pyrimidin-5-yl)-allyl]-2,2,2-trifluoroacetamide This is treated with ozone to give the aldehyde or the carboxylic acid, depending on workup. The first cyclizes spontaneously, and is reduced to give a product that presents the puDDA hydrogen bonding pattern. The acid is cyclized with DCC in tetrahydrofuran to give a product that presents the puDDA hydrogen bonding pattern.

4-Amino-3-hydro-7-(3,5-di-O-toluoyl-2-deoxy-beta-D-ribofuranosyl)-pyrrolo[2,3-d]pyrimidin-2-one 2-Methoxy-7-(3,5-di-O-toluoyl-2-deoxy-beta-D-ribofuranosyl)-pyrrolo[2,3-d]pyrimidin-4-ylamine (3.135 g, 6.06 mmol) is suspended in dry ethylene glycol (20 mL) at room temperature. Benzenethiol (3 mL, 29.2 mmol) is then added, and the mixture is heated at 100-120° C. (but not above 130° C.). The reaction is monitored for consumption of starting material by TLC (1-3 days). When no more starting nucleoside remains, the mixture is cooled to room temperature, and ethyl acetate (150 mL) is added. The resulting solution is transferred to an Erlenmeyer flask and sodium tetraborate decahydrate (37.0 g, 97 mmol) is added as a powder. The mixture is stirred for 5 min., after which the supernatant is decanted and the solid mixture washed with ethyl acetate (3×50 mL). The organic fractions are combined, concentrated in vacuo and chromatographed using gradients of methylene chloride, methanol and ammonium hydroxide (conc. aqueous) (50:1:0.2—methylene chloride:methanol:ammonium hydroxide to 50:3.5:0.2 using methylene chloride:methanol:ammonium hydroxide) yields the product as an off-white semisolid that can be recrystallized from methylenechloride/hexanes.

4-(N,N-Diisobutyl-formamidine)-3-hydro-7-(3,5-di-O-toluoyl-2-deoxy-β-D-ribofuranosyl)-pyrrolo[2,3-d]pyrimidin-2-one 4-Amino-3-hydro-7-(3,5-di-O-toluoyl-2-deoxy-β-D-ribofuranosyl)-pyrrolo[2,3-d]pyrimidin-2-one (1.014 g, 2.02 mmol) is dissolved in $CH_2Cl_2$ (10 mL), Dimethoxymethyldiisobutylamine (2.5 mL of a 70% w/w solution in diisobutylformamide) is added dropwise. The solution is allowed to stir at room temperature overnight. The mixture is concentrated to small bulk (yellow oil) and resolved by chromatography using gradients of methylene chloride and methanol to afford a mixture of the two isomers. The mixture is then repurified to resolve the two isomers.

2'-Deoxy-$N^6$-diisobutylaminomethylidene-7-deazaisoguanosine

Compound 1 (0.807 mmol) is coevaporated with DMF and dissolved in anhydrous DMF (5 mL). N,N-Diisobutylformamide dimethyl acetal (1.4 equiv., 1.58 mmol, 321 mg) is added and the mixture stirred at room temperature for 6.5 h. The mixture is then concentrated in vacuum and the residue purified by column chromatography (silica gel, $CHCl_3$/17.5% MeOH).

2'-Deoxy-$N^6$-diisobutylaminomethylidene-3',5'-bis(trimethylsilyl)-7-deaza-isoguanosine. The product from above (0.775 mmol) is coevaporated with dry pyridine and dissolved in anhydrous THF (15 mL). Triethylamine (3 equiv., 2.32 mmol, 0.323 mL) and TMSCl (3 equiv.) are added and the mixture is stirred at room temperature (15 h). MeOH (2 mL) is added and the mixture concentrated in vacuum and partitioned (dilute $NaHCO_3$ solution/ethyl acetate). The organic layer is isolated, dried ($Na_2SO_4$) and evaporated to give product, which is used without further purification.

2'-Deoxy-$N^6$-diisobutylaminomethylidene-$O^2$—N,N-diphenylcarbamoyl-3',5'-bis(trimethylsilyl)7-deaza-isoguanosine The product from above (0.596 mmol) is coevaporated with pyridine and dissolved in anhydrous pyridine (10 mL). N,N-Diphenylcarbamoyl chloride (2 equiv.,) and N,N-diisopropylethylamine (1.7 equiv., 1.01 mmol, 0.176 mL) are added and the mixture is stirred at room temperature for 4 h. MeOH (1 mL) is then added and the mixture concentrated in vacuum, and partitioned ($NaHCO_3$/$CHCl_3$). The organic layer is dried ($Na_2SO_4$) and the solvent evaporated. The product was purified by column chromatography ($CH_2Cl_2$/1.5% MeOH).

2'-Deoxy-$N^6$-diisobutylaminomethylidene-$O^2$—N,N-diphenylcarbamoyl-7-deaza-isoguanosine The compound from above (0.445 mmol) is dissolved in THF (10 mL). TBAF (2.2 equiv., 0.98 mmol, 0.98 mL 1M solution in THF) is added. The mixture is stirred at room temperature for 1.5 h, concentrated in vacuum, and extracted (water/$CHCl_3$). The organic layer is dried ($Na_2SO_4$) and the solvent evaporated to yield the product, which is purified by column chromatography ($CHCl_3$/10% MeOH).

2'-Deoxy-$N^6$-diisobutylaminomethylidene-5'-dimethoxytrityl-$O^2$—N,N-diphenylcarbamoyl-7-deaza-isoguanosine The product from above (2.08 mmol) is coevaporated with dry pyridine, dissolved in anhydrous pyridine (50 mL) and DMAP (0.25 equiv.), DMTCl (1.8 equiv.,) and $Et_3N$ (3 equiv.) are added. The mixture is stirred at room temperature for 4.5 h, MeOH (5 mL) is added and the solution is concentrated in vacuum. The residue is diluted with ethyl acetate, extracted (aqueous NaHCO$_3$ solution/ethyl acetate), the organic layers are recovered, and the combined organic layers dried (Na$_2$SO$_4$), the solvent evaporated and the residue purified by column chromatography (silica gel, CHCl$_3$/1.5% MeOH, then 10% MeOH) to give product.

2'-Deoxy-N$^6$-diisobutylaminomethylidene-5'-dimethoxytrityl-O$^2$—N,N-diphenylcarbamoylisoguanosine, 3'-[(2-cyanoethyl)-(N,N-diisopropyl)]-phosphoramidite The compound from above (0.199 mmol) is dissolved in CH$_2$Cl$_2$ (3 mL). The solution is cooled to 0° C. N,N-Diisopropylethylamine (5.5 equiv.) and 2-cyanoethyl N,N-diisopropylphosphoramido-chloridite (1.1 equiv.) are added. The solution is stirred at room temperature for 30 min. Aqueous NaHCO$_3$ is added and the resulting mixture is extracted with CH$_2$Cl$_2$/2% Et$_3$N. The combined organic layers were dried (Na$_2$SO$_4$), the solvent evaporated and the residue purified by column chromatography (silica gel, hexanes/CHCl$_3$/ethyl acetate/triethylamine 60:20:20:10, then 40:25:25:10. This product was obtained as a light yellow foam. The product was dissolved in CH$_2$Cl$_2$/10% Et$_3$N and added dropwise into stirred hexanes. The resulting precipitate is dried under vacuum.

3'-O-Acetyl-2'-deoxy-5-O-dimethoxytrityl-N$^6$-diisobutylaminomethylidene-O$^2$—N,N-diphenylcarbamoyl-7-deaza-isoguanosine The tritylated species having a free 3'-OH group (1.01 mmol), DMAP (0.25 equiv.), Et$_3$N (2.5 equiv.), and acetic anhydride (1.2 equiv., 1.2108 mmol, 0.114 mL) are added to a solution of dry pyridine (30 mL). The mixture is stirred at room temperature for 2 h. MeOH (1 mL) is added, the mixture concentrated in vacuum, extracted (EtOAc/dilute aqueous NaHCO$_3$), the organic layer dried (Na$_2$SO$_4$), the solvent evaporated and the residue used in the next step without further purification.

3'-O-Acetyl-2'-deoxy-N$^6$-diisobutylaminomethylidene-O$^2$—N,N-diphenylcarbamoyl7-deaza-isoguanosine The compound from the previous step is dissolved in a solution of MeOH (5 mL) and CHCl3 (1 mL). The solution is cooled to 0° and 10% anhydrous HCl in MeOH (5 mL) is added. Stirring is continued at 0° for 5 min. The reaction mixture is then neutralized with aqueous NaHCO$_3$ and extracted (CHCl$_3$). The resulting organic layer is dried (Na$_2$SO$_4$) and the solvent is evaporated. The product is isolated by column chromatography (CHCl$_3$/5% MeOH).

2'-Deoxy-7-deaza-isoguanosine triphosphate

The product from above (0.170 mmol) is coevaporated with pyridine and dissolved in an anhydrous mixture of pyridine (0.17 mL) and dioxane (0.51 mL). 2-Chloro-4H-1,3,2-benzodioxaphosphorin-4-one (1.1 equiv.) dissolved in dioxane (0.18 mL) is added and a white precipitate forms. The reaction mixture is stirred at room temperature for 10 minutes. Tri-n-butylammonium pyrophosphate (1.5 equiv.) in DMF (0.6 mL) and tri-n-butylamine (4.2 equiv.) is added, immediately forming a clear solution. The solution is stirred for 10 minutes. A solution (1%) of iodine in pyridine/water (98:2) is added (3.74 mL). Stirring is continued for 15 minutes. Excess iodine is destroyed by addition of 5% aqueous sodium sulfite. Water (6 mL) is added, the mixture is stirred for 30 min. Aqueous ammonia (25%, 30 mL) is added followed by stirring at room temperature for 5 h. The solvent is then evaporated and the residue purified by ion exchange chromatography on DEAE Sephadex. Further purification was achieved by reversed phase HPLC.

Tritylation (Alternative Procedure)

The protected nucleoside analog (8.7 mmol) is dissolved in dry pyridine (150 mL). To the solution is added 4',4"-dimethoxytrityl chloride (1.2 equiv). The reaction mixture is stirred at room temperature for 24 hours. The reaction is quenched by the addition of water (3 mL). The solution is concentrated under vacuum, and an aqueous solution of NaHCO$_3$ (80 mL) is added. The mixture is extracted with EtOAc, dried (Na$_2$SO$_4$), the solvents evaporated under reduced pressure, and the product isolated by column chromatography (chloroform/acetone 9:1, then 9:2).

Phosphoramidite (Alternative Procedure)

The protected derivative from above (0.12 mmol) is dissolved in CH$_3$CN (2.0 mL). The solution is then treated with bis-(N,N-diisopropylamino)-3-cyanoethyloxyphosphine (Aldrich, 1.2 equiv.), and diisopropylammonium tetrazolide (0.06 mmol), following a literature procedure] McBride, L. J., Kierzek, R., Beaucage, S. L. & Caruthers, M. H. (1986) *J. Am. Chem. Soc.* 108, 2040-2048]. The progress of the reaction was monitored by TLC (SiO$_2$ eluted with EtOAc:CH$_2$Cl$_2$: triethylamine 45:45:10). An additional portion (0.02 mL) of bis-(N,N-diisopropylamino)-3-cyanoethyloxyphosphine was then added, and stirring continued for an additional hour. Water (2 drops) was added, the mixture stirred for 15 min, the mixture diluted with CH$_2$Cl$_2$ (30 mL), and the organic layer washed with aqueous Na$_2$CO$_3$ (2%) and dried (Na$_2$SO$_4$). The phosphoramidite (120.3 mg, 93%) was isolated by chromatography (SiO$_2$, EtOAc:CH$_2$Cl$_2$:triethylamine 45:45:10 as eluant). $^{31}$P-NMR 149.7 (doublet of diastereomers).

3'-O-(Acetyl) Derivative of the Nucleoside Analog

The dimethoxytritylated nucleoside analog from above (0.200 mmol) is coevaporated with dry pyridine (0.8 mL). The residue is redissolved in pyridine (1 mL) under dry Ar. Acetic acid anhydride (10 equiv) is added dropwise, and the reaction mixture is stirred for 3 h. The solution is then cooled on an ice bath, and the reaction is quenched by addition of methanol (1 mL). The solvents are evaporated under reduced pressure. The remaining foam is coevaporated with dry toluene (1 mL), and the residue is dissolved in a mixture of trifluoroacetic acid and CH$_2$Cl$_2$ (2% v/v, 10 mL total volume). The mixture is then stirred for 30 min, at which point saturated aqueous NaHCO$_3$ solution (5 mL) is added. The phases are separated, the aqueous phase isolated, and the aqueous phase extracted with CH$_2$Cl$_2$. The combined organic phases are concentrated under reduced pressure, and the remaining yellowish oil is resolved by chromatography on silica gel (CH$_2$Cl$_2$/MeOH 98:2) to afford the 3'-O-acetyl derivative of the nucleoside, with its 5'-OH group free.

5'-O-Triphosphate Derivative of the Nucleoside Analog

The 3'-acetylated nucleoside analog (0.162 mmol) is then coevaporated again with dry pyridine (1 mL). The residue is then redissolved in a mixture of dry pyridine (162 μL) and dry 1,4-dioxane (486 μL) under Ar. A freshly prepared solution of 2-chloro-4H-1,3,2-benzodioxaphosphorin-4-one (1 M) in 1,4-dioxane (162 μL, 1.0 equiv) is then added to the stirred reaction mixture. A white precipitate forms immediately. After 10 minutes, a well vortexed emulsion of tributylammonium pyrophosphate (110 mg) in DMF/tri-n-butylamine (3:1, 648 μL) is quickly added. This causes the precipitate to dissolve immediately. After 10 minutes of incubation at room temperature, a 1% solution of iodine in pyridine/water (98:2, 3.24 mL) is added dropwise. After 15 min following completed addition of the iodine solution, the solvents are removed at 40° C. under reduced pressure. The remaining brown oil is dissolved in water/MeOH (1:1, 10 mL), and the mixture is allowed to stand for 30 minutes. Then, a portion of solution of aqueous concentrated ammonia (20 mL) is added, the solution turns turbid. The suspension is stirred for 1 h, the solvents are removed at 40° C. under reduced pressure, and the remaining light brown oil is coevaporated with water. Water/acetonitrile (95:5, 2 mL) is then added to yield a light brown suspension. The unsoluble components are removed by filtration (0.2µ cellulose acetate membrane) to yield a clear, slightly yellow, filtrate containing the triphosphate. The triphosphate is purified by chromatography (DEAE Sephadex, 30 mL, 1.5×18 cm, TEAB 0.1 M to 0.8 M (linear gradient) in the presence of 10% acetonitrile). Further purification is done by reversed phase RP-HPLC (Column: Nova-Pak HR C18 cartridge (Waters), 6µ, 25×100 mm. Solvent A: triethylammonium acetate (25 mM, pH 7.0), solvent B: acetonitrile. Flow rate: 5.5 mL/min. Gradient: 0-1 min 100% A, 10 min 13% B (linear), 55 min 18% B (linear)). The eluate is lyophilized to dryness, and the residue is redissolved in water. Dissolution and lyophilization is done three more times, to remove the residual triethylammonium acetate. The triphosphate is stored at −20° C., either as 5 mM solution in water or as a lyophilized powder. The triphosphate can be recognized by characteristic signals in the $^{31}P$ NMR in $D_2O$ solvent (121 MHz: δ relative to phosphoric acid=−7.9 (poorly resolved doublet), −9.1 (doublet), and −20.6 (triplet) ppm).

The heterocyclic system carrying an amino acid side chain, or an aminomethyl side chain, can be prepared in analogous form using the appropriately substituted nitrohistidine as a starting material. The starting materials for this synthesis are described in:

[Tautz, W., Teitel, S., Brossi, A. (1973) Nitrohistidines and nitrohistamines. *J. Med. Chem.* 16(6), 705-7]. [Sehgal, Raj K. (1991) Synthesis of nitroimidazoles having acetyl function in the imidazole nucleus. *J. Praktische Chemie* (*Leipzig*), 333 (4), 665-8].

Oligonucleotide Analogs

Oligonucleotide analogs containing non-standard nucleotide are prepared by "trityl off" solid-phase synthesis using an Applied Biosystems automated DNA synthesizer from the (β-cyanoethyl protected phosphoramidites. They are purified by polyacrylamide gel electrophoresis (12-20%). Chemicals are from Glen Research, while the DNA membrane columns (0.2 µmol scale) and CPG columns (1.0 µmol scale) containing the 3'-terminal nucleoside are from PerSeptive Biosystems.

Vials to contain the protected phosphoramidite of the nucleoside analog are rinsed with acetone and immediately placed into an oven at 150° C. to dry overnight. The vials are then cooled to room temperature in a dessicator over $P_2O_5$ under vacuum of <1 torr. The dessicator is vented with dry Ar, and phosphoramidite is placed into the vials. If only a small amount of phosphoramidite is available, the compound is transferred into the prepared vial as solution in $CH_2Cl_2$, and the solvent is evaporated under reduced pressure. Subsequently, the vials containing the phosphoramidites are returned to the desiccator with $P_2O_5$ to be stored under vacuum. The desiccator is vented with dry Ar, and the vials are immediately closed and stored in a dessicator containing anhydrous $MgSO_4$ until needed.

Directly before oligonucleotide synthesis, the phosphoramidites are dissolved in anhydrous acetonitrile (0.15 g/1.5 mL). Standard phosphoramidites are used as solutions in anhydrous acetonitrile (0.5 g/10 mL) at half the concentration that is recommended by the synthesizer manufacturer. Synthesis on a 0.2-1.0 µmol scale is performed using a standard synthesis protocol, with the exception of an extended coupling time (600 s) for the analog.

After the synthesis is complete (0.2-1.0 µmol scale), the column material (CPG beads) is transferred into a 1.5 mL microcentrifuge tube with sealed screw cap. Upon addition of conc. $NH_4OH$ solution (1 mL), the tube is shaken in an Eppendorf shaker at maximum speed overnight at 55° C. After the mixture had been centrifuged for a few seconds, the supernatant is transferred into a clean microfuge tube. The column material is washed with water (250 µL), and the supernatant is combined with the first supernatant. The solvent is evaporated from the combined supernatants by means of a speed vac at ambient temperature. The residue is dissolved in NaOAc solution (0.7 M, pH 5.2, 300 µL). An occasionally occurring cloudy precipitation is removed by filtration through a syringe filter with cellulose acetate membrane (pore size 0.2 µm). Ice cold EtOH (1 mL) is added to the clear solution. After vortexing, the mixture is stored at −20° C. for several hours. The mixture is then centrifuged at 4° C. and 14,000 rpm for 30 min, and the supernatant is removed. The remaining pellet is washed with 80% aqueous EtOH (1 mL) by gentle shaking, and the mixture is centrifuged again at 4° C. and 14,000 rpm for 10 min. After removal of the supernatant, the oligonucleotide pellet is dried by exposure to the air and redissolved in water (500 µL).

The oligonucleotide analog is purified by either HPLC that is obtained after above described post synthetic processing is mixed with PAGE loading buffer (1:1). The mixture is incubated at 95° C. for 2 min and immediately loaded onto the preheated polyacrylamide gel. Up to ¼ of a 0.2 µmol synthesis or ¹/₂₀ of a 1.0 µmol synthesis is loaded into one well. Electrophoresis is performed at 45-55 W, maintaining a gel temperature of 55-60° C. When the desired oligonucleotides had migrated ca. 25 cm as judged by the dye markers, electrophoresis is stopped. The oligonucleotide bands are visualized by UV quenching with the help of a silica gel coated TLC plate containing a fluorescence indicator. The desired bands are cut out with a razor blade. Usually the slowest migrating band of a crude mixture corresponded to the desired full length product. The gel pieces are transferred into tubes of appropriate size and crushed with the help of a pipette tip. NaOAc solution (300 mM, pH 7.5) is added to completely cover the gel particles. The mixture is shaken vehemently on a vortexer for 5 h to overnight. After centrifugation, the supernatant is removed. The gel particles are shaken with a fresh portion of NaOAc solution (300 mM, pH 7.5) for a few hours. The supernatant is filtered and combined with the supernatant from the first extraction. The combined supernatants are filtered through a cellulose acetate membrane (pore size 0.2 µm). The oligonucleotide is recovered from the filtrate by EtOH precipitation. The pellet is washed with 70% EtOH. The so obtained oligonucleotides are pure enough for all subsequent applications. They are stored as solutions in water (3-250 pmol/µL) at −20° C.

The concentrations of the oligonucleotide solutions are determined via measurement of the UV absorbance of the oligonucleotide solution at λ=260 nm.

The relation between UV absorbance and the amount of the oligonucleotide (in nanomoles) present in the sample is given approximately by the formula $A_{260}*100/n$=nmole oligonucleotide, where $A_{260}$ is the absorbance at λ=260 nm in OD, and n is the number of bases of the oligonucleotide. This formula is employed for both standard and functionalized oligonucleotides without consideration of the extinction coefficient of the functionalized bases.

Oligonucleotide analogs are analyzed by anion exchange HPLC under the following conditions:

Column: Dionex

Solvent A: Sodium phosphate (20 mM, pH 6.0), solvent B: Sodium phosphate (20 mM, pH 6.0), NaCl (1 M), solvent C: ACN.

Gradient: 0-1 min 75% A/25% C, 30 min 55% B/25% C (linear).

For purification of large amounts of oligonucleotides (up to 10 OD), a larger column with the same packing material is used. The gradients are adjusted to keep the $R_t$ value about constant. On the preparative scale, the oligonucleotides are further purified and desalted on a larger column (Nova-Pak HR® C18 cartridge (Waters), 6 μm 60 Å, 25×100 mm, flow rate 5.5 mL/min). Chromatography times are extended by 5 min.

Oligonucleotide analogs containing the nucleotide analog are characterized by MALDI-TOF mass spectrometry. Short oligonucleotides (9-10mers) are in addition analyzed by electrospray ionization mass spectrometry (ESI MS). The oligonucleotide is injected as solution in isopropanol/water (1:1) containing TEA (30 mM).

The oligonucleotide analogs can be further analyzed by enzymatic degradation. The analog is dissolved in water/acetonitril mixtures (9:1, 4.0 μL). Digestion buffer (0.1 M Tris-HCl, pH 8.3, 20 mM MgCl$_2$, 4.0 μL) and 10 mM Zn(OAc)$_2$ solution (1.0 μL) is then added, followed by phosphodiesterase I (1.0 μL, 0.0006 U), nuclease P1 (14, 0.0006 U) and alkaline phosphatase, diluted with digestion buffer (1.0 μL, 1.5 U). The mixture is incubated at 50° C. for 5 h. The sample is then diluted with triethylammonium acetate buffer (1 M, pH 7.0, 20 μL) and water/acetonitrile (9:1, 70 μL), filtered and analyzed using RP-HPLC (Column: Adsorbosphere, Solvent A: TEAOAc (25 mM, pH 7.0), solvent B: solvenacetonitrile 4:1, solvent C: acetonitrile. The composition of the oligonucleotide is verified by using the integrated absorbance of the component nucleosides at 260 nm In this fashion, the following oligonucleotides are prepared:

A Molecular Beacon Containing the Disclosed Nucleoside Analog and its Complement in the Stem, SEQ ID 4 Fl-5'-<u>YTYYR</u>TGTGTTTTCTACAAGCTGATG<u>YRRAR</u>-3'-Qu SEQ ID 2

R represents the nucleoside analog 1 incorporated into a DNA strand. Y represents the complement, in this example isocytidine, a small complement to R that presents a hydrogen bond acceptor-acceptor-donor pattern. A, T, G, and C represent the 2'-deoxyribonucleotides as generally disclosed in the literature. Fl is a fluorescent moiety, in this example rhodamine. Qu is a fluorescence quencher moiety, here DABCYL.

An Oligonucleotide Analog Suitable for Immobilization Using Avidin Analogs.

SEQ ID 2 5'-biotin-<u>YTYYR</u>TGTGTTTTCTACAAGCT GATG SEQ ID 2 where R represents the nucleoside analog 1 incorporated into a DNA strand. Y represents the complement, in this example isocytidine, a small complement to R that presents a hydrogen bond acceptor-acceptor-donor pattern. A, T, G, and C represent the 2'-deoxyribonucleotides as generally disclosed in the literature. Fl is a fluorescent moiety. Qu is a fluorescence quencher moiety. This is able to mediate the capture of the following oligonucleotide to a solid support, which may be a two dimensional array, a one dimensional array, or a bead:

SEQ ID 1 3'-<u>RARRY</u>ACACAAAAGATGTTCGACTACAAAAAAGA SEQ ID 1

The process of the capture is performed at room temperature in phosphate buffer (0.1 mM, pH 7.0) in the presence of NaCl (500 mM).

A Primer-Template Combination.

SEQ ID 2 5'-<u>YTYYR</u>TGTGTTTTCTACAAGCTGATG-3' SEQ ID 2 (primer)

SEQ ID 3 3'-<u>ACACAAAAGATGTTCGACTA-CAAAAARY</u>GACTTGTACAT-5'SEQID3(template)

Enzymic Synthesis of Oligonucleotide Analogs Containing the Disclosed Nucleoside Analog Under the Direction of a Template.

Primer Extension Experiments.

In a typical primer extension experiment, 5'-$^{32}$P-labeled primer having the sequence shown below:

SEQ ID 2 5'-<u>YTYYR</u>TGTGTTTTCTACAAGCTGATG-3' SEQ ID 3 (primer)

SEQ ID 3 3'-<u>ACACAAAAGATGTTCGACTA-CAAAAARY</u>GACTTGTACAT-5'SEQID3(template)

where R represents the nucleoside analog 1 incorporated into a DNA strand, Y represents the complement, in this example isocytidine, a small complement to R that presents a hydrogen bond acceptor-acceptor-donor pattern, and A, T, G, and C represent the 2'-deoxyribonucleotides as generally disclosed in the literature.

The template, in this example, has the sequence shown above (656 nM of the primers, 920 nM of the templates). The reaction is run in the buffer appropriate for the polymerase or reverse transcriptase supplier (sold by the polymerase or reverse transcriptase supplier). Here, the polymerase is the double mutant of HIV reverse transcriptase described by Sismour et al. [op. cit.]. The components are mixed with dATP, dGTP, dCTP, TTP and dQTP (Q is the nucleoside analog, either R or Y, all triphosphates at a final concentration 130 μM each) in a total volume of 160 μL. After heating the mixture to 95° C. for 1 min, the primer/template complex is annealed by cooling slowly to room temperature over 1 h. Primer extension is started by addition of the polymerase (16 μL). The mixture is then incubated at the optimal temperature for the polymerase. Aliquots (25 μL), taken at various times during the elongation reaction, are quenched by addition of a premixed solution of sodium acetate (2.5 μL, 3 M, pH 5.2), EDTA (1 μL, 0.5 M, pH 8), and ethanol (50 μL). After being stored at −20° C. for 20 min, the samples are centrifuged (14,000 rpm, 4° C., 20 min) and the pellets dried in the vacuum concentrator. The residues are redissolved in PAGE loading buffer and the samples separated on a 10% PAGE gel (7 M urea). The gel is analyzed using the MolecularImager®.

To improve reproducibility in cases where multiple reactions are run in parallel, a master mixture of primer/template and the dNTPs is prepared by scaling up the listed procedure. Master mixtures are not stored for more than 24 hours at −20° C.

Standing Start Experiments.

The primer (15 pmol, 5'-$^{32}$P-labeled) and template (21 pmol) are incubated with polymerase at the conditions specified by the supplier, with the volume adjusted with water to 21 μL with water. The DNA is denatured (95° C., 1 min) and cooled to room temperature over a period of 1 hour. After addition of the appropriate dNTPs (1.67 μL, 130 μM final concentration of each) and an aliquot of the double mutant of HIV reverse transcriptase described by Sismour et al. [op. cit.]. (0.2 U), the mixture is incubated for up to 30 min at 37° C. The reaction is quenched by addition of a premixed solution of sodium acetate (2.5 μL, 3 M, pH 5.2), EDTA (1 μL, 0.5 M, pH 8), and EtOH (50 μL), the DNA is recovered by centrifugation, and the pellet is dried in the vacuum concentrator. The DNA is dissolved in PAGE loading buffer (bromophenol blue/xylene cyanol mix 0.1 g, water, 1 mL, and formamide, 4 mL) and analyzed using a 10% PAGE gel (7 M urea). The gel is analyzed with the MolecularImager®.

Enzymic Synthesis of a Library of Random Sequence Oligonucleotide Analogs Containing the Non-Standard Nucleotide Using Terminal Transferase, not Under the Direction of a Template.

In a 1.5-mL Eppendorf-tube is added:

| | |
|---|---|
| 1. Water | 642.0 μL |
| 2. Cacodylate buffer (5x conc.) | 200.0 μL |
| 3. MgCl$_2$ (100 mM) | 80.0 μL |
| 4. CoCl$_2$ (100 mM) | 40.0 μL |
| 5. dNTP-Mix (each 10 mM dATP, dCTP, dGTP, TTP, and dQTP) | 25.0 μL |

The final concentration is each triphosphate is 0.25 mM, the are total 1 mM triphosphate.

| | |
|---|---|
| 6. Seq1 (20) (113 pmol/μL, = total 1 nmol) | 8.9 μL |
| 7. Terminal transferase (25 units/μL, = total 100 units) | 4.0 μL |

The sodium cacodylate-trihydrate buffer is prepared by dissolving (2.14 g, 10 mmol) in ca. 5 mL of water. Tris•HCl buffer (1.25 mL, 1.0 M, pH 8.0), 1.25 mL acetylated bovine serum albumin (10 mg/mL, New England Biolabs) and water are mixed to a final volume of 10 mL. The pH is adjusted at 6.6 by adding a few drops of concentrated HCl and the stock solution sterilized by ultrafiltration. The mixture is stored at −20° C.

Prior to the reaction mixture is shaken briefly and incubated for 16 hours at 37° C. In the beginning the solution is clear, a white precipitate is observed to form, presumably cobalt pyrophosphate. To stop the reaction, the tube is placed on ice and diluted with 0.1 volume of an EDTA solution (200 mM in water, pH=8). The reaction mixture is divided into four Eppendorf tubes and the DNA is precipitated with ethanol (addition of 0.11 volumes of 3.0 M NaOAc. pH=5.4 and 2.5 volumes of ethanol. The mixture is stored at −20° C. overnight, centrifuged at 4° C. for 30 min, the supernatant is removed by pipette and discarded. The precipitate is washed with 500 μl of 70% ethanol, dried for 2 hours in air at RT, and dissolved in 100 μl water to yield a solution of ≦1 nmol DNA "Seq 1-random" (21) in 400 μl water.

The DNA oligos are analyzed by agarose gel electrophoresis (2% agarose in TAE-buffer, ethidium bromide) using pBR 322 MspI-digestion as markers. The sample consisted of 5.0 μl DNA-solution (≦1 nmol 21 in 400 μl water) plus 1.0 μl gel loading buffer III (6× conc.). The gel is developed (30 min, 76 V), and visualized under ultraviolet light (l=254 nm). The gel of the mixture of oligodeoxyribonucleotides 21 displayed (as expected) no sharp bands, but rather a "smeared" band with a center at ca. 300 nt, and visibly extending from 200 to 600 nt.

Example 8

Immobilization of an Oligonucleotide Analog Incorporating the Disclosed Nucleoside Analog onto a Microsphere, or Bead A biotinylated oligonucleotide analog is captured onto a solid support carrying immobilized avidin. Other methods for immobilization include the "click chemistry" reaction of an azido moiety on the oligonucleotide analog to an alkene or alkyne on the support (or vice versa), or the reaction of an aniline moiety attached to the oligonucleotide analog with a diazo unit on the support (for example). Other methods for immobilization involve the entrapment of the oligonucleotide analog in a gel, such as a thermoresponsive gel or in a colony.

Example 9

Process of Using Oligonucleotide Analogs Containing the Disclosed Nucleoside Analog for the Purpose of Binding to a Complementary Nucleotide Analogs Here, the two oligonucleotides that are completely, or nearly completely, complementary, as defined by the expanded set of Watson-Crick pairing rules, are mixed in aqueous solution at a temperature and salt concentration where the paired duplex is expected to be stable. In general, for oligonucleotide analogs from 8-100 nucleotides in length, this corresponds to pH's between 5 and 9, salt concentrations from 100 mM to 1 M, and temperatures between 0 and 80° C.

Example 10

Immobilization of an Oligonucleotide Analog Incorporating the Disclosed Nucleoside Analog onto a Two Dimensional Array In this example, the support is a two dimensional array. Analogous processes use a one dimensional array, a Luminex bead, a magnetic microsphere, or a quantum dot as the solid support. In general, for oligonucleotide analogs from 8-100 nucleotides in length, this corresponds to pH's between 5 and 9, salt concentrations from 100 mM to 1 M, and temperatures between 0 and 80° C.

Example 11

Amplification of an Oligonucleotide Analog Incorporating the Disclosed Nucleoside Analog in a Polymerase Chain Reaction To facilitate strand separation, one of the PCR primers (P2-C6) is designed to contain a tetranucleotide appended to the 5'-position via two C6 polyethyleneglycol units. This made the product derived from the primer move slower in a gel electrophoresis experiment than the product derived from the reverse primer.

Template T2-pyDAD (50 pmol) is mixed with 5'-radiolabeled primer P2-C6 (750 pmol), primer P1-RS (750 pmol), dATP, dTTP, dCTP, dGTP, d(puADA)TP, d(pyDAD)TP (final conc. 200 µM each), HIV RT buffer (333 µL, 3×), and the reaction volume adjusted to 1 mL with water. The mixture is heated to 95° C. (10 ml) and allowed to cool to ambient temperature (1 h). HIV RT (Y188L,E478Q) (10 U) is added to the reaction mixture, which is then incubated at 37° C. for 24 hours. An aliquot (5 µL) is removed and quenched with 20 mM EDTA in formamide (5 µL). The remaining reaction mixture is heated again to 95° C. for 10 minutes and again cooled to ambient temperature over 1 hour. Another aliquot of RT is then added. This cycle is repeated 4 times. The products from each round of PCR amplification are resolved using a 12% PAGE gel (7 M urea). The gel is analyzed using the MolecularImager software. A positive control experiment is run under the same conditions while substituting T-2 for T2-pyDAD.

The PCR reaction is quenched with EDTA (final conc. 10 mM) and the DNA isolated via ethanol (2.5 mL) precipitation and subsequently washed with 70% ethanol in water. The dry pellet is dissolved in PAGE loading buffer and analyzed by electrophoresis on a 20% PAGE gel (7 M urea). The product generated from full extension of primer P2-C6 is longer, and therefore moved slower, than the product generated from the full extension of P2-Rev. The product from full extension of P2-C6 is cut from the gel and extracted by incubating in a crush and soak buffer (0.1% SDS, 0.5 M NH$_4$OAc, 10 mM Mg(OAc)$_2$) at 37° C. overnight. The solution is filtered through a Millipore filter (0.45 µm pore size) and the DNA recovered by ethanol precipitation. The DNA pellet (T1-X-PCR) is dissolved in water to a final concentration of 10 µM.

Example 12

Incorporation of the Disclosed Nucleoside Analog into a Dendrimeric Structure Based on Branched DNA The process follows literature in the prior art for oligonucleotide analogs that do not incorporate the nucleoside of the instant invention. [Collins, M. L., Irvine, B., Tyner, D., Fine, E., Zayati, C., Chang, C. A., Horn, T., Ahle, D., Detmer, J., Shen, L. P., Kolberg, J., Bushnell, S., Urdea, M. S., Ho, D. D. (1997) *Nucl. Acids Res.* 25, 2979-2984.]

Example 13

Incorporation of the Disclosed Nucleoside Analog into a Dendrimeric Structure that Incorporates Non-Nucleosidic Components Oligonucleotide analogs synthesized as described above are incorporated into DNA dendrimers, following the procedure disclosed in the literature, where this literature disclosure does not describe dendrimers with containing the nucleoside analog of the instant invention, but rather Is constructed from all standard nucleotides. [Lowe M, Spiro A, Zhang Y Z, Getts R (2004) Multiplexed, particle-based detection of DNA using flow cytometry with 3DNA dendrimers for signal amplification. *Cytometry Part A* 60A, 135-144] [Wang J, Jiang M, Nilsen T W, Getts R C (1998) Dendritic nucleic acid probes for DNA biosensors. *J. Am. Chem. Soc.* 120, 8281-8282] [Hudson RHE, Robidoux S, Damha M J (1998) Divergent solid-phase synthesis of nucleic acid dendrimers *Tetrahedron Lett.* 39, 1299-1302] [Hudson R H E, Damha M J (1993) nucleic-acid dendrimers—novel biopolymer structures. *J. Am. Chem. Soc.* 115, 2119-2124].

These are used in a multiplexed, flow cytometric assay, using fluorescence detection. The analyte consists of single-stranded (ss) DNA amplicons that are hybridized to capture probes on the surface of fluorescent polystyrene microspheres (beads) and that are labeled with streptavidin-R-phycoerythrin (single-step labeling). These beads have a low reporter fluorescence background and high efficiency of DNA hybridization. The DNA/SA-RPE complex is then labeled with dendrimers and SA-RPE. The bead complexes were detected with a Luminex 100 flow cytometer. Bead standards were developed to convert the intensity to the number of SA-RPE labels per bead and the number of dendrimers per bead.

What is claimed is:

1. A composition of matter comprising molecules having the structure

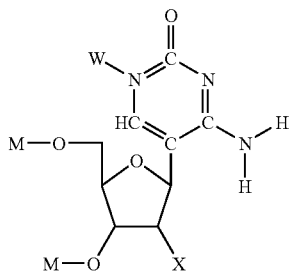

Wherein X is independently selected from the group consisting of H, OH, O-Me, and O-allyl, M is independently selected from the group consisting of H, phosphate, a protecting group, a phosphoramidite, diphosphate, triphosphate and phosphate ester, and W is any substituent other than hydrogen.

2. A composition of matter comprising molecules having the structure

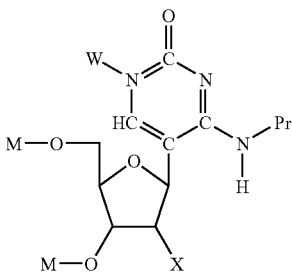

wherein X is independently selected from the group consisting of H, an oxygen protected in a form suitable for RNA synthesis, O-Me, and O-allyl, M is independently selected from the group consisting of H, phosphate, a protecting group, a phosphoramidite, diphosphate, diphosphate and phosphate ester, Pr is a protecting group, and W is any substituent other than hydrogen.

3. An oligonucleotide where at least one of the nucleotide units is replaced by a nucleoside analog having the structure

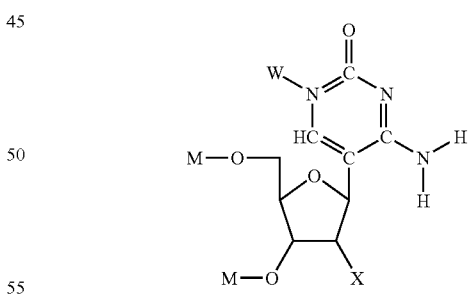

wherein X is independently selected from the group consisting of H, an oxygen protected in a form suitable for RNA synthesis, O-Me, and O-allyl, M is independently selected from the group consisting of H, phosphate, a protecting group, a phosphoramidite, diphosphate, triphosphate and phosphate ester, and W is any substituent other than hydrogen.

* * * * *

UNITED STATES PATENT AND TRADEMARK OFFICE
CERTIFICATE OF CORRECTION

| | | |
|---|---|---|
| PATENT NO. | : 7,741,294 B1 | |
| APPLICATION NO. | : 11/371756 | |
| DATED | : June 22, 2010 | |
| INVENTOR(S) | : Steven Albert Benner | |

It is certified that error appears in the above-identified patent and that said Letters Patent is hereby corrected as shown below:

Please correct.

Columns 41 & 42, Claim 1, 2 and 3 formulas should read,

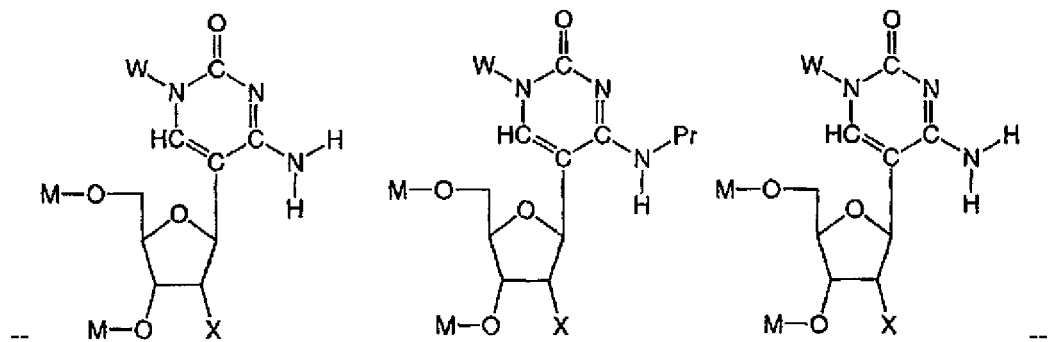

Signed and Sealed this
Fourth Day of January, 2011

David J. Kappos
*Director of the United States Patent and Trademark Office*

SEQUENCE LISTING

```
<160> NUMBER OF SEQ ID NOS: 4

<210> SEQ ID NO 1
<211> LENGTH: 34
<212> TYPE: DNA
<213> ORGANISM: Artificial sequence
<220> FEATURE:
<221> NAME/KEY: misc_feature
<222> LOCATION: (30)..(30)
<223> OTHER INFORMATION: a nonstandard nucleotide of the instant
      invention
<220> FEATURE:
<221> NAME/KEY: misc_feature
<222> LOCATION: (31)..(31)
<223> OTHER INFORMATION: a nonstandard nucleotide of the instant
      invention
<220> FEATURE:
<221> NAME/KEY: misc_feature
<222> LOCATION: (32)..(32)
<223> OTHER INFORMATION: a nonstandard nucleotide of the instant
      invention
<220> FEATURE:
<221> NAME/KEY: misc_feature
<222> LOCATION: (34)..(34)
<223> OTHER INFORMATION: a nonstandard nucleotide of the instant
```

-continued

```
      invention
<220> FEATURE:
<223> OTHER INFORMATION: Synthetic

<400> SEQUENCE: 1
agaaaaaaca tcagcttgta gaaaacacay rrar                                    34

<210> SEQ ID NO 2
<211> LENGTH: 26
<212> TYPE: DNA
<213> ORGANISM: Artificial sequence
<220> FEATURE:
<221> NAME/KEY: misc_feature
<222> LOCATION: (1)..(1)
<223> OTHER INFORMATION: a nonstandard nucleotide of the instant
      invention
<220> FEATURE:
<221> NAME/KEY: misc_feature
<222> LOCATION: (3)..(3)
<223> OTHER INFORMATION: a nonstandard nucleotide of the instant
      invention
<220> FEATURE:
<221> NAME/KEY: misc_feature
<222> LOCATION: (4)..(4)
<223> OTHER INFORMATION: a nonstandard nucleotide of the instant
      invention
<220> FEATURE:
<221> NAME/KEY: misc_feature
<222> LOCATION: (5)..(5)
<223> OTHER INFORMATION: a nonstandard nucleotide of the instant
      invention
<220> FEATURE:
<223> OTHER INFORMATION: Synthetic

<400> SEQUENCE: 2
ytyyrtgtgt tttctacaag ctgatg                                             26

<210> SEQ ID NO 3
<211> LENGTH: 38
<212> TYPE: DNA
<213> ORGANISM: Artificial sequence
<220> FEATURE:
<221> NAME/KEY: misc_feature
<222> LOCATION: (12)..(12)
<223> OTHER INFORMATION: a nonstandard nucleotide of the instant
      invention
<220> FEATURE:
<221> NAME/KEY: misc_feature
<222> LOCATION: (13)..(13)
<223> OTHER INFORMATION: a nonstandard nucleotide of the instant
      invention
<220> FEATURE:
<223> OTHER INFORMATION: Synthetic

<400> SEQUENCE: 3
tacatgttca gyraaaacat cagcttgtag aaaacaca                                38

<210> SEQ ID NO 4
<211> LENGTH: 31
<212> TYPE: DNA
<213> ORGANISM: Artificial sequence
<220> FEATURE:
<221> NAME/KEY: misc_feature
<222> LOCATION: (1)..(1)
<223> OTHER INFORMATION: a nonstandard nucleotide of the instant
      invention
<220> FEATURE:
<221> NAME/KEY: misc_feature
<222> LOCATION: (3)..(3)
<223> OTHER INFORMATION: a nonstandard nucleotide of the instant
      invention
<220> FEATURE:
<221> NAME/KEY: misc_feature
```

```
<222> LOCATION: (4)..(4)
<223> OTHER INFORMATION: a nonstandard nucleotide of the instant
      invention
<220> FEATURE:
<221> NAME/KEY: misc_feature
<222> LOCATION: (5)..(5)
<223> OTHER INFORMATION: a nonstandard nucleotide of the instant
      invention
<220> FEATURE:
<221> NAME/KEY: misc_feature
<222> LOCATION: (27)..(27)
<223> OTHER INFORMATION: a nonstandard nucleotide of the instant
      invention
<220> FEATURE:
<221> NAME/KEY: misc_feature
<222> LOCATION: (28)..(28)
<223> OTHER INFORMATION: a nonstandard nucleotide of the instant
      invention
<220> FEATURE:
<221> NAME/KEY: misc_feature
<222> LOCATION: (29)..(29)
<223> OTHER INFORMATION: a nonstandard nucleotide of the instant
      invention
<220> FEATURE:
<221> NAME/KEY: misc_feature
<222> LOCATION: (31)..(31)
<223> OTHER INFORMATION: a nonstandard nucleotide of the instant
      invention
<220> FEATURE:
<223> OTHER INFORMATION: Synthetic

<400> SEQUENCE: 4
ytyyrtgtgt tttctacaag ctgatgyrra r                             31
```